US011237177B2

United States Patent
McGrane et al.

(10) Patent No.: US 11,237,177 B2
(45) Date of Patent: Feb. 1, 2022

(54) METHODS FOR IDENTIFYING MODULATORS OF GPR92

(71) Applicant: MARS, INCORPORATED, McLean, VA (US)

(72) Inventors: Scott Joseph McGrane, Leicestershire (GB); Matthew Ronald Gibbs, Leicestershire (GB); Richard Masten Fine, Oradell, NJ (US); Boris Klebansky, Oradell, NJ (US)

(73) Assignee: MARS, INCORPORATED, McLean, VA (US)

( * ) Notice: Subject to any disclaimer, the term of this patent is extended or adjusted under 35 U.S.C. 154(b) by 341 days.

(21) Appl. No.: 16/093,046

(22) PCT Filed: Apr. 14, 2017

(86) PCT No.: PCT/US2017/027626
§ 371 (c)(1),
(2) Date: Oct. 11, 2018

(87) PCT Pub. No.: WO2017/181008
PCT Pub. Date: Oct. 19, 2017

(65) Prior Publication Data
US 2019/0170772 A1 Jun. 6, 2019

Related U.S. Application Data

(60) Provisional application No. 62/322,601, filed on Apr. 14, 2016.

(51) Int. Cl.
G01N 33/53 (2006.01)
G01N 33/74 (2006.01)
C07K 14/705 (2006.01)
C07K 14/00 (2006.01)

(52) U.S. Cl.
CPC ............ G01N 33/74 (2013.01); C07K 14/00 (2013.01); C07K 14/705 (2013.01); G01N 2333/726 (2013.01); G01N 2500/04 (2013.01)

(58) Field of Classification Search
None
See application file for complete search history.

(56) References Cited

U.S. PATENT DOCUMENTS

| 2003/0017528 | A1* | 1/2003 | Chen ................... C07K 14/723 435/69.1 |
| 2009/0274684 | A1 | 11/2009 | Griffin et al. |
| 2012/0276563 | A1 | 11/2012 | Wieland |
| 2013/0247233 | A1 | 9/2013 | Gaitanaris et al. |

FOREIGN PATENT DOCUMENTS

| EP | 0075463 A3 | 9/1984 |
| EP | 0750849 A1 | 1/1997 |
| JP | H0614711 A | 1/1994 |
| JP | 2006-513702 A | 4/2006 |
| JP | 2013-512664 A | 4/2013 |
| RU | 2 577 409 C2 | 3/2016 |
| WO | WO 2004/040000 A2 | 5/2004 |
| WO | WO 2005/119263 A2 | 12/2005 |
| WO | WO 2006/003877 A1 | 1/2006 |
| WO | 2006040534 A2 | 4/2006 |
| WO | WO 2011/067202 A1 | 6/2011 |
| WO | WO 2012/028243 A1 | 3/2012 |
| WO | WO 2014/199114 A1 | 12/2014 |

OTHER PUBLICATIONS

Bystrova, et al., "Functional expression of the extracellular-Ca2+—sensing receptor in mouse taste cells", Journal of Cell Science, vol. 123, Issue 6, pp. 972-982, Mar. 2010.
Clemmensen, et al., "The GPCR, class C, group 6, subtaype A (GPRCA6A) receptor: from cloning to physiological function", British Journal of Pharmacology, Mar. 2014, 171(S):1129-1141.
Faure, et al., "Molecular determinants of non-competitive antagonist binding to the mouse GPRC6A receptor", Cell Calcium, vol. 46, Issues 5-6, Nov.-Dec. 2009, pp. 323-332 (Abstract only).
Wellendorph, et al., "Deorphanization of GPRC6A: A Promiscuous I-α-Amino Acid Receptor with Preference for Basic Amino Acids", Molecular Pharmacology Mar. 2005, 67 (3) 589-597 (Abstract Only).
Wellendorph, et al., "Molecular basis for amino acid sensing by family C G-protein-coupled receptors", British Journal of Pharmacology, vol. 156, Issue 6, Mar. 2009, p. 869-884.
Wellendorph, et al., "Molecular cloning, expression, and sequence analysis of GPRC6A, a novel family C G-protein-coupled receptor", Gene, vol. 335, Jun. 23, 2004, pp. 37-46 (Abstract only).
Wellendorph, et al., "The rat GPRC6A: Cloning and characterization", Gene, vol. 396, Issue 2, Jul. 15, 2007, pp. 257-267 (Abstract only).
Choi et al., "Identification of a protein hydrolysate responsive G protein-coupled receptor in enterocytes," Am. J. Physiol. Gastrointest. Liver Physiol., 292:G98-G112 (2007).
Cline, "Perspectives for Gene Therapy: Inserting New Genetic Information into Mammalian Cells by Physical Techniques and Viral Vectors," Pharmac. Ther. 29:69-92 (1985).

(Continued)

Primary Examiner — Michael D Pak
(74) Attorney, Agent, or Firm — Baker Botts L.L.P.

(57) ABSTRACT

The present disclosure provides methods for identifying compounds that modulate the activity and/or expression of GPR92, wherein said compounds can be incorporated into flavor compositions that can be used to modify the taste and/or palatability of pet food products. In certain non-limiting embodiments, the present disclosure provides a method for identifying a composition that modulates the activity of a GPR92 receptor comprising (a) contacting a test agent with a GPR92 receptor, (b) determining the activity of the GPR92 receptor, and (c) selecting as the composition, a test agent that increases the activity of the GPR92 receptor.

18 Claims, 25 Drawing Sheets
Specification includes a Sequence Listing.

(56) References Cited

OTHER PUBLICATIONS

Cohen et al., "Receptor-Mediated Transport of DNA into Eukaryotic Cells," Meth. Enzymol. 217:618-644 (1993).
Cunningham et al., "High-Resolution Epitope Mapping of hGH-Receptor Interactions by Alanine-Scanning Mutagenesis," Science 244:1081-1085 (1989).
Eswar et al., "Comparative Protein Structure Modeling Using Modeller," Curr Protoc Bioinformatics (Supplement 15):5.6.1-5.6.30, 30 pages (2006).
Haid et al., "Gustatory sensory cells express a receptor responsive to protein breakdown products (GPR92)," Histochem. Cell Biol., 140:137-145 (2013).
International Search Report dated Jul. 5, 2017 in International Application No. PCT/US2017/027626.
Karlin et al., "Applications and statistics for multiple high-scoring segments in molecular sequences," Proc. Natl. Acad. Sci. USA 90:5873-5877 (1993).
Karlin et al., "Methods for assessing the statistical significance of molecular sequence features by using general scoring schemes," Proc. Natl. Acad. Sci. USA 87:2264-2268 (1990).
Lee et al., "Structural insights into ligand recognition and selectivity for class A, B, and C GPCRs," Eur J Pharmacol. Sep. 15, 2015;763(Pt B):196-205. Epub May 14, 2015.
Loeffler et al., "Gene Transfer into Primary and Established Mammalian Cell Lines with Lipopolyamine-Coated DNA," Meth. Enzymol. 217:599-618 (1993).
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25(17):3389-3402 (1997).
Berman et al., "The Protein Data Bank," Nucleic Acids Research 28(1):235-242 (2000).
Cartoni et al., "Taste Preference for Fatty Acids Is Mediated by GPR40 and GPR120," J. Neurosci., 30(25):8376-8382 (2010).
Choi et al., "GPR93 activation by protein hydrolysate induces CCK transcription and secretion in STC-1 cells," Am. J. Physiol. Gastrointest. Liver Physiol., 292:G1366-G1375 (2007).
Cotten et al., "Receptor-Mediated Transport of DNA into Eukaryotic Cells," Meth. Enzymol. 217:618-644 (1993).
Pearson et al., "Improved tools for biological sequence comparison," Proc. Natl. Acad. Sci. USA 85:2444-2448 (1988).
Torelli et al., "ADVANCE and ADAM: two algorithms for the analysis of global similarity between homologous informational sequences," CABIOS 10(1):3-5 (1994).
Williams et al., "Unique Ligand Selectivity of the GPR92/LPA5 Lysophosphatidate Receptor Indicates Role in Human Platelet Activation," The Journal of Biological Chemistry 284(25):17304-17319 (2009).
Yang et al., "The I-TASSER Suite: protein structure and function prediction," Nature Methods 12(1):7-8 (2015).
Oh et al., "Identification of Farnesyl Pyrophosphate and N-Arachidonylglycine as Endogenous Ligands for GPR92," Journal of Biological Chemistry, 283(30):21054-21064 (2008).
Pontius et al., "Initial sequence and comparative analysis of the cat genome," Genome Research, 17(11):1675-1689 (2007).
Li et al., "The sequence and de novo assembly of the giant panda genome," Nature, 463(7279):311-317 (2010).

\* cited by examiner

FIGURE 1

Feline GPR92 Nucleotide Sequence (SEQ. ID NO.: 1)

ATGTTGCCCAACTCTACCAACAGTTCTGTTCCCCCTGCCAACGGTTCTGTTCCCCGTGCCC
CGACTACCGGCCCACCCACCGCCTGCACATGGTGGCCTACAGCCTGGTGCTGGCCGCAGGGC
TCCCCCTCAACGCGCTGGCCCTCTGGGTCTTCCTGCGCGCGCTGCGAGTGCACTCCGTCGTG
AGCGTGTACATGTGCAACCTGGCGGCCAGCGACCTGCTCTTCACCCTCTCGCTGCCCGTGCG
CATCTCCTACTACGCCCTGCACTACTGGCCCTTCTCCGACCTCCTGTGCCAGACGGCGGGCG
CCATCTTCCAGACGAACATGTACGGCAGCTGCATCTTCCTGACTCTCATCAACGTGGACCGC
TACGCGGCCATCGTGCACCCGCTGCGGCTGCGCCACCTGCGGCGGCCCCGCGTGGCGCGGCT
GCTCTGCCTGGGAGTGTGGGCGCTCATCCTCGTGTTCGCTGTGCCCACCGTCCTGGTGCACA
GGCCCTCGTCCTGCAGCTACGGCGGCGGCCAGGTGCGCCTGTGCTTCGAGAGCTTCGGCGAC
AGGCTGTGGAAGGGCGGGCTGCTGCCGCTCGTGCTGCTGGCCGAGGCGCTGGGCTTCCTGCT
GCCCCTGGTGGCGGTGCTCTACTCGTCGGGCCGGGTCTTCTGGACCCTGGCGCGGCCCGACG
CCACGCAGAGCCAGCGGCGGCGGAAGACCGTGCGCCTCCTGCTGGCCAACCTCGTCATCTTC
CTGCTGTGCTTCGTGCCCTACAACGCCACGCTGGCGGTGTACGGGCTGCTGCGGGGCAACCT
GGTGGCGGCGAACAGCAAGGTCTGCGATCGGGTGCGCGGGGTGCTGATGGTGATGGTGCTGT
TGGCCGGCGCCAACTGCGTGCTAGACCCTCTGGTGTATTACTTCAGCGCCGAGGGTTTCCGC
AACACCCTGCGAGGCCTGGGCACTCCGAACCGCGCCAGGACCTTGGCCACCAACGGGGCTCA
GGGGGCGCTCGCCGAACAGCCCACTGAGACCACTTACATCACCACCCCGGCTACCGCCGAAC
AGGGGCTGCTCAGGCCCTCCAACGTGGGGACACCCTTAACCCAGCTCCCCGAGGACTCGGCC
CTCTGA

FIGURE 2

Canine GPR92 Nucleotide Sequence (SEQ. ID NO.: 2)

```
ATGCTGACCGCCTCGGCCAACAGCTCCGTCCCCCCATGCCCCGACTACCGGGTCACCCACCG
CCTGCACATGGTGGCCTACAGCCTGGTGCTGGCCGCGGGGCTCCCCCTCAACGCGCTGGCCC
TCTGGGTCTTCCTGCGCGCGCTGCGCGTGCACTCCGTGGTCAGCGTGTACATGTGCAACCTG
GCGGCCAGCGACCTGCTCTTCACGCTCTCGCTGCCCGTGCGCATCTCCTACTACGCCCTGCA
CCACTGGCCCTTCTCCGACCTCCTGTGTCAGACGGCCGGCGCCGTCTTCCAGACCAACATGT
ACGGCAGCTGCATCTTCCTGACCCTCATTAACGTGGACCGCTACGCGGCCATCGTGCACCCA
CTGCGGCTGCGCCACCTGCGGCGGCCCCGCGTGGCGCGGCTGCTGTGCCTGGGCGTGTGGGC
GCTCATCCTGGTGTTCGCCGTGCCCACCGTCCTGGTGCACCGGCCCTCGCCCTGCAGCTACG
ACGGCGGCCGGGCGCGGCTGTGCTTCGAGAGCTTCGGCGACAAGCTGTGGAAGGGCGGGCTG
CTGCCGCTCGTGCTGCTGGCCGAGGCGCTGGGCTTCCTGCTGCCGCTCGCGGCCATGCTCTA
CTCGTCGGGCCGGGTCTTCTGGACCCTGGCGCGGCCCGACGCCACGCGGAGCCGGCGGCGGC
GGAAGACCGTGCGCCTCCTGCTGGCCAACCTCGTCATCTTCCTGCTGTGCTTCGTGCCCTAC
AACGCCACGCTGGCCGTCTACGGGCTGCTGCGGGCAACCTGGTGGCGGCCGGCAGCGAGGC
CAGCGACCGCGTGCGCCAGGTGCTCATGGTGATGGTGCTGCTGGCCAGCGCCAACTGCGTGC
TGGACCCGCTGGTGTACTACTTCAGCGCCGAGGGCTTCCGCAACACCCTGCGCGGCCTGGGC
ACTTGGCACCGTGCCAGGACCTTGGCCACCAACGGGGCGCAGGGGCGCTGGCCGAGCGGCT
CACCGAGACCACCTGCATCGCCGGGCCGGCTCCCGCCAGCCGAGAGCCTCCCGCGTCCTCCC
CCGGGGGGACGCCCTTGACCCAGCGCCGGGAGGACTCGGCCCTCTGA
```

FIGURE 3

Human GPR92 Nucleotide Sequence (SEQ. ID NO.: 3)

ATGTTAGCCAACAGCTCCTCAACCAACAGTTCTGTTCTCCCGTGTCCTGACTACCGACCTAC
CCACCGCCTGCACTTGGTGGTCTACAGCTTGGTGCTGGCTGCCGGGCTCCCCCTCAACGCGC
TAGCCCTCTGGGTCTTCCTGCGCGCGCTGCGCGTGCACTCGGTGGTGAGCGTGTACATGTGT
AACCTGGCGGCCAGCGACCTGCTCTTCACCCTCTCGCTGCCCGTTCGTCTCTCCTACTACGC
ACTGCACCACTGGCCCTTCCCCGACCTCCTGTGCCAGACGACGGGCGCCATCTTCCAGATGA
ACATGTACGGCAGCTGCATCTTCCTGATGCTCATCAACGTGGACCGCTACGCCGCCATCGTG
CACCCGCTGCGACTGCGCCACCTGCGGCGGCCCCGCGTGGCGCGGCTGCTCTGCCTGGGCGT
GTGGGCGCTCATCCTGGTGTTTGCCGTGCCCGCCGCCCGCGTGCACAGGCCCTCGCGTTGCC
GCTACCGGGACCTCGAGGTGCGCCTATGCTTCGAGAGCTTCAGCGACGAGCTGTGGAAAGGC
AGGCTGCTGCCCCTCGTGCTGCTGGCCGAGGCGCTGGGCTTCCTGCTGCCCCTGGCGGCGGT
GGTCTACTCGTCGGGCCGAGTCTTCTGGACGCTGGCGCGCCCCGACGCCACGCAGAGCCAGC
GGCGGCGGAAGACCGTGCGCCTCCTGCTGGCTAACCTCGTCATCTTCCTGCTGTGCTTCGTG
CCCTACAACAGCACGCTGGCGGTCTACGGGCTGCTGCGGAGCAAGCTGGTGGCGGCCAGCGT
GCCTGCCCGCGATCGCGTGCGCGGGGTGCTGATGGTGATGGTGCTGCTGGCCGGCGCCAACT
GCGTGCTGGACCCGCTGGTGTACTACTTTAGCGCCGAGGGCTTCCGCAACACCCTGCGCGGC
CTGGGCACTCCGCACCGGGCCAGGACCTCGGCCACCAACGGGACGCGGGCGGCGCTCGCGCA
ATCCGAAAGGTCCGCCGTCACCACCGACGCCACCAGGCCGGATGCCGCCAGTCAGGGGCTGC
TCCGACCCTCCGACTCCCACTCTCTGTCTTCCTTCACACAGTGTCCCCAGGATTCCGCCCTC
TGA

FIGURE 4

Feline GPR92 Amino Acid Sequence (SEQ. ID NO.: 4)

MLPNSTNSSVPPANGSVPPCPDYRPTHRLHMVAYSLVLAAGLPLNALALWVFLRALRVHSVV
SVYMCNLAASDLLFTLSLPVRISYYALHYWPFSDLLCQTAGAIFQTNMYGSCIFLTLINVDR
YAAIVHPLRLRHLRRPRVARLLCLGVWALILVFAVPTVLVHRPSSCSYGGGQVRLCFESFGD
RLWKGGLLPLVLLAEALGFLLPLVAVLYSSGRVFWTLARPDATQSQRRRKTVRLLLANLVIF
LLCFVPYNATLAVYGLLRGNLVAANSKVCDRVRGVLMVMVLLAGANCVLDPLVYYFSAEGFR
NTLRGLGTPNRARTLATNGAQGALAEQPTETTYITTPATAEQGLLRPSNVGTPLTQLPEDSA
L*

FIGURE 5

Canine GPR92 Amino Acid Sequence (SEQ. ID NO.: 5)

```
MLTASANSSVPPCPDYRVTHRLHMVAYSLVLAAGLPLNALALWVFLRALRVHSVVSVYMCNL
AASDLLFTLSLPVRISYYALHHWPFSDLLCQTAGAVFQTNMYGSCIFLTLINVDRYAAIVHP
LRLRHLRRPRVARLLCLGVWALILVFAVPTVLVHRPSPCSYDGGRARLCFESFGDKLWKGGL
LPLVLLAEALGFLLPLAAMLYSSGRVFWTLARPDATRSRRRRKTVRLLLANLVIFLLCFVPY
NATLAVYGLLRGNLVAAGSEASDRVRQVLMVMVLLASANCVLDPLVYYFSAEGFRNTLRGLG
TWHRARTLATNGAQGALAERLTETTCIAGPAPASREPPASSPGGTPLTQRREDSAL*
```

FIGURE 6

Human GPR92 Amino Acid Sequence (SEQ. ID NO.: 6)

MLANSSSTNSSVLPCPDYRPTHRLHLVVYSLVLAAGLPLNALALWVFLRALRVHSVVSVYMC
NLAASDLLFTLSLPVRLSYYALHHWPFPDLLCQTTGAIFQMNMYGSCIFLMLINVDRYAAIV
HPLRLRHLRRPRVARLLCLGVWALILVFAVPAARVHRPSRCRYRDLEVRLCFESFSDELWKG
RLLPLVLLAEALGFLLPLAAVVYSSGRVFWTLARPDATQSQRRRKTVRLLLANLVIFLLCFV
PYNSTLAVYGLLRSKLVAASVPARDRVRGVLMVMVLLAGANCVLDPLVYYFSAEGFRNTLRG
LGTPHRARTSATNGTRAALAQSERSAVTTDATRPDAASQGLLRPSDSHSLSSFTQCPQDSAL
*

FIGURE 7

METHODS FOR IDENTIFYING MODULATORS OF GPR92

CROSS-REFERENCE TO RELATED APPLICATION

This application is a U.S. National Stage Patent Application under 35 U.S.C. § 371 of International Application No. PCT/US2017/027626, filed on Apr. 14, 2017, which claims priority to U.S. Provisional Application Ser. No. 62/322,601 filed on Apr. 14, 2016, the contents of each of which are incorporated by reference in their entireties, and to which priority is claimed.

FIELD

The presently disclosed subject matter relates to methods for identifying compounds that modulate the activity and/or expression of GPR92.

SEQUENCE LISTING

The specification further incorporates by reference the Sequence Listing submitted herewith via EFS on Oct. 11, 2018. Pursuant to 37 C.F.R. § 1.52 (e)(5), the Sequence Listing text file, identified as seqlistingGPR92.txt, is 14,614 bytes and was created on Oct. 10, 2018. The Sequence Listing, electronically filed herewith, does not extend beyond the scope of the specification and thus does not contain new matter.

BACKGROUND

Taste profiles for edible compositions include basic tastes such as sweet, salt, bitter, sour, umami and kokumi. Taste profiles have also been described as including free fatty acid tastes. Chemical compounds that elicit these tastes are often referred to as tastants. Without being bound by theory, it is hypothesized that tastants are sensed by taste receptors in the mouth and throat which transmit signals to the brain where the tastants and resulting taste profiles are registered. Taste receptors include GPR92 (also known as GPR93 and LPAR5), which is a member of Class A of G-protein coupled receptors (GPCRs) (also known as rhodopsin-like GPCRs). GPR92 has been shown to be expressed in gustatory sensory cells (see Haid et al., Histochem. Cell Biol., 140(2): 137-145 (2013)), and can be activated by protein hydrolysates i.e., products of protein hydrolysis (peptone) (see Choi et al., Am. J. Physiol. Gastrointest. Liver Physiol., 292: G98-G112 (2007); Choi et al. Am. J. Physiol. Gastrointest. Liver Physiol., 292 (5): G1366-75 (2007)).

Pet food manufacturers have a long-standing desire to provide pet food products that have high nutritional value. In addition, and with particular regard to cat and dog foods, pet food manufacturers desire a high degree of palatability so that pets can receive the full nutritional benefit from their food. Domestic animals, especially cats, are notoriously fickle in their food preferences, and often refuse to eat a pet food product that it has accepted over time or refuse to eat any more than a minimal amount of a pet food product. This phenomenon may be, in part, due to the subtle differences in the sensory profiles of the raw material, which can be perceived by the domestic animals because of their gustatory and olfactory systems. As a result, pet owners frequently change types and brands of pet food in order to maintain their pets in a healthy and contented condition.

While there have been recent advances in taste and flavor technologies, there remains a need for compounds that can enhance or modify the palatability of pet food products by enhancing or modifying the taste, texture and/or flavor profiles of the pet food product. The enhancement or modification can be to increase the intensity of a desirable attribute, to replace a desirable attribute not present or somehow lost in the pet food product, or to decrease the intensity of an undesirable attribute. In particular, it is desirable to increase the intensity of a desirable tastant in a pet food product.

Therefore, there remains a need in the art for methods to identify compounds that enhance the palatability and/or modulate the taste of pet food products and for flavor compositions comprising these compounds.

SUMMARY OF THE INVENTION

The presently disclosed subject matter provides methods for identifying compounds that enhance, increase and/or modulate the activity of a GPR92 receptor. Once identified, such compounds can be comprised in a flavor composition that can be added to a variety of pet food products to increase the palatability of the products. For example, in certain embodiments of the present disclosure, such a flavor composition is combined with a pet food product in an amount effective to increase the taste and/or palatability of the pet food product.

In certain embodiments, a method for identifying compounds that enhance, increase and/or modulate the activity and/or expression of a GPR92 receptor comprises expressing a GPR92 receptor having a nucleotide sequence set forth in SEQ ID NO: 1, 2 or 3, or a fragment or variant thereof, in a cell. The method can further comprise contacting the cell expressing the GPR92 receptor with a test compound and determining the activity and/or expression of the GPR92 receptor in the presence of the compound as compared to the activity and/or expression of the receptor in the absence of the compound.

In certain embodiments, a method for identifying compounds that enhance, increase and/or modulate the activity of a GPR92 receptor comprises expressing a GPR92 receptor having an amino acid sequence set forth in SEQ ID NO: 4, 5 or 6, or a fragment or variant thereof, in a cell. The method can further comprise contacting the cell expressing the GPR92 receptor with a test compound and determining the activity and/or expression of the GPR92 receptor in the presence of the compound as compared to the activity and/or expression of the receptor in the absence of the compound.

In certain embodiments, the cell expressing the GPR92 also expresses a calcium-binding photoprotein. In certain embodiments, the calcium-binding photoprotein is selected from the group consisting of clytin, aequorin, obelin and combinations thereof.

In certain embodiments, the present disclosure provides a method for identifying a composition that modulates the activity of a GPR92 receptor comprising (a) contacting a test agent with a GPR92 receptor, (b) determining the activity of the GPR92 receptor, and (c) selecting as the composition, a test agent that increases the activity of the GPR92 receptor.

In certain embodiments, the present disclosure provides a method for identifying a composition that modulates the activity of a GPR92 receptor comprising (a) contacting a test agent with a GPR92 receptor, (b) detecting an interaction between the test agent and one or more amino acids in a 7 Transmembrane (7TM) domain of the GPR92 receptor, and (c) selecting as the composition, a test agent that interacts with one or more of the amino acids.

In certain embodiments, the amino acids that a modulatory compound interacts with comprise one or more of Arg83 on Helix 2; Gly103, Phe106, Gln107, Met110, and/or Cys114 on Helix 3; Thr161 and/or His165 on Helix 4; Ala200, Gly204, and/or Pro208 on Helix 5; Phe248, Phe252, Tyr255, Asn256, and/or Leu259 on Helix 6; Arg281, Met285, and/or Val288 on Helix 7; and/or Glu182 on the second extracellular (EC2) loop, and combinations thereof, of a GPR92 receptor, for example, a feline GPR92 receptor, for example, as described by SEQ ID NO: 4.

In certain embodiments, the amino acids that a modulatory compound interacts with comprise one or more of Arg83, Arg281, Tyr255, and combinations thereof, of a GPR92 receptor, for example, a feline GPR92 receptor, for example, as described by SEQ ID NO: 4.

In certain embodiments, the amino acids that a modulatory compound interacts with comprise one or more of Arg76 on Helix 2; Gly96, Phe99, Gln100, Met103, and/or Cys107 on Helix 3; Thr154 and/or His158 on Helix 4; Ala193, Gly197, and/or Pro201 on Helix 5; Phe241, Phe245, Tyr248, Asn249, and/or Leu252 on Helix 6; Arg274, Met278, and/or Val281 on Helix 7; and/or Glu175 on the EC2 loop, and combinations thereof, of a GPR92 receptor, for example, a canine GPR92, for example, as described by SEQ ID NO: 5.

In certain embodiments, the amino acids that a modulatory compound interacts with comprise one or more of Arg76, Arg274, Tyr248, and combinations thereof, of a GPR92 receptor, for example, a canine GPR92 receptor, for example, as described by SEQ ID NO: 5.

In certain embodiments, the interaction is determined by site directed mutagenesis, x-ray crystallography, x-ray spectroscopy, Nuclear Magnetic Resonance (NMR), cross-linking assessment, mass spectroscopy, electrophoresis, displacement assay, and combinations thereof.

In certain embodiments, the present disclosure provides a method for identifying a composition that modulates the activity of a GPR92 receptor comprising (a) contacting a GPR92 agonist with a GPR92 receptor, (b) determining the activity of the GPR92 receptor, (c) contacting a test agent with the GPR92 receptor, (d) determining the activity of the GPR92 receptor, and (e) selecting the test agent as the composition when the activity of (d) is greater than the activity of (b).

In certain embodiments, the GPR92 receptor agonist is selected from the group consisting of NAG (N-Arachidonylglycine), FPP (3,7,11-Trimethyl-2,6,10-dodecatrien-1-yl pyrophosphate), LPA (18:0) (1-stearoyl-2-hydroxy-sn-glycero-3-phosphate), CPA (18:1) (1-oleoyl-sn-glycero-2,3-cyclic-phosphate), LPA (14:0) (1-myristoyl-2-hydroxy-sn-glycero-3-phosphate), LPA (16:0) (1-palmitoyl-2-hydroxy-sn-glycero-3-phosphate), LPA (18:1) (1-oleoyl-2-hydroxy-sn-glycero-3-phosphate), farnesyl monophosphate (FMP), alkyl-glycerophosphate (AGP, also known as alkyl-LPA), cyclic phosphatidic acid (CPA); carba-CPA (CCPA), 2-carba-CPA (2CCPA), or 3-carba-CPA (3CCPA) and combinations thereof.

In certain embodiments, the GPR92 receptor is expressed by a cell, and wherein the test agent is contacted to the cell. In certain embodiments, the cell expresses a calcium-binding photoprotein. In certain embodiments, wherein the calcium-binding photoprotein is selected from the group consisting of clytin, aequorin, obelin, any recombinant or isolated versions thereof, and any combinations thereof. In certain embodiments, intracellular calcium levels are monitored by a luminescence detection or a fluorescence detection. In certain embodiments, the calcium sensitive fluorescent dye is selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1 shows a feline GPR92 nucleotide sequence (SEQ ID NO: 1).

FIG. 2 shows a canine GPR92 nucleotide sequence (SEQ ID NO: 2).

FIG. 3 shows a human GPR92 nucleotide sequence (SEQ ID NO: 3).

FIG. 4 shows a feline GPR92 amino acid sequence (SEQ ID NO: 4).

FIG. 5 shows a canine GPR92 amino acid sequence (SEQ ID NO: 5).

FIG. 6 shows a human GPR92 amino acid sequence (SEQ ID NO: 6).

FIG. 7 shows the sequence alignment of the amino acid sequences of a feline, canine, and human GPR92.

DETAILED DESCRIPTION

Figure 8:
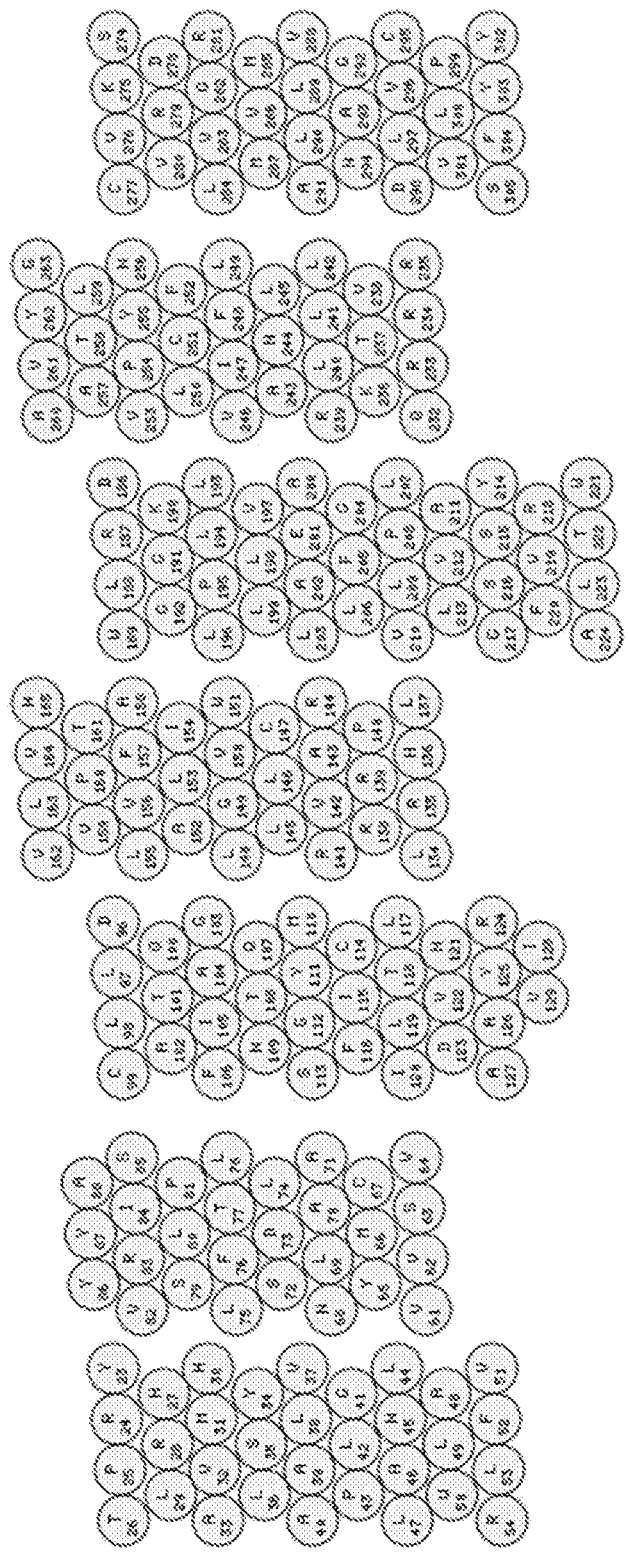
FIG. 8 shows the helix plot of the 7TM domain of feline GPR92.

The presently disclosed subject matter relates to methods for identifying compounds that modulate the activity and/or expression of GPR92, wherein said compounds can be included in a flavor composition that can be used to increase the palatability and/or enhance or modify the taste of various pet food products such as a nutritionally-complete pet food or pet treats.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation of receptor cells in a subject's taste buds. In certain embodiments, taste can be selected from the group consisting of sweet, sour, salt, bitter, kokumi and umami. In certain embodiments, "taste" can include free fatty acid taste. See, e.g., Cartoni et al., J. of Neuroscience, 30(25): 8376-8382 (2010), the contents of which are incorporated herein by reference. In certain embodiments, a taste is elicited in a subject by a "tastant." In certain embodiments, a tastant can be a synthetic tastant. In certain embodiments, the tastant is prepared from a natural source.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical, or any combination thereof.

As used interchangeably herein, "aroma" and "smell" refer to an olfactory response to a stimulus. For example, and not by way of limitation, an aroma can be produced by aromatic substances that are perceived by the odor receptors of the olfactory system.

As used herein, "flavor profile" refers to a combination of sensory stimuli, for example, tastes, such as sweet, sour, bitter, salty, umami, kokumi, free fatty acid tastes, and/or olfactory, tactile and/or thermal stimuli. In certain embodiments, flavor profiles comprise one or more flavors which contribute to the sensory experience of a subject. In certain embodiments, modifying, changing or varying the combination of stimuli in a flavor profile can change the sensory experience of a subject.

As used herein, "palatability" can refer to the overall willingness of an animal to eat a certain food product. Increasing the "palatability" of a pet food product can lead to an increase in the enjoyment and acceptance of the pet food by the companion animal to ensure the animal eats a "healthy amount" of the pet food. The term "healthy amount" of a pet food as used herein refers to an amount that enables the companion animal to maintain or achieve an intake contributing to its overall general health in terms of micronutrients, macronutrients and calories, such as set out in the "Mars Petcare Essential Nutrient Standards." In certain embodiments, "palatability" can mean a relative preference of an animal for one food product over another. For example, when an animal shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. Palatability can be determined by a standard testing protocol in which the animal has equal access to both food products such as a test called "two-bowl test" or "versus test." Such preference can arise from any of the animal's senses, but can be related to, inter alia, taste, aftertaste, smell, mouth feel and/or texture.

The term "pet food" or "pet food product" means a product or composition that is intended for consumption by a companion animal, such as cats, dogs, guinea pigs, mice, rabbits, birds and horses. For example, but not by way of limitation, the companion animal can be a "domestic" cat such as *Felis domesticus*. In certain embodiments, the companion animal can be a "domestic" dog, e.g., *Canis lupus familiaris*. A "pet food" or "pet food product" can include any food, feed, snack, food supplement, liquid, beverage, treat, toy (chewable and/or consumable toys), meal substitute or meal replacement.

As used herein "nutritionally-complete" refers to pet food products that contain all known required nutrients for the intended recipient of the pet food product, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, flavor composition includes one or more excipients.

As used herein, the terms "modulates" or "modifies" refers an increase or decrease in the amount, quality or effect of a particular activity of a receptor and/or an increase or decrease in the expression, activity or function of a receptor. "Modulators," as used herein, refer to any inhibitory or activating compounds identified using in silico, in vitro and/or in vivo assays for, e.g., agonists, antagonists and their homologs, including fragments, variants and mimetics.

"Inhibitors" or "antagonists," as used herein, refer to modulating compounds that reduce, decrease, block, prevent, delay activation, inactivate, desensitize or downregulate biological activity and/or expression of receptors or pathway of interest.

"Inducers," "activators" or "agonists," as used herein, refer to modulating compounds that increase, induce, stimulate, open, activate, facilitate, enhance activation, sensitize or upregulate a receptor or pathway of interest.

In certain embodiments, an "active compound" is a compound that modulates, i.e., is active against, a GPR92 receptor. For example, an active compound can be active against the GPR92 receptor as an agonist, antagonist, positive allosteric modulator (PAM), negative allosteric modulator, or by showing a mix of activities, for example, agonist activity as well as positive allosteric modulation activity, or agonist activity as well as negative allosteric modulation activity.

As used herein, the terms "vector" and "expression vector" refer to DNA molecules that are either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes. Vectors are often recombinant molecules containing DNA sequences from several sources.

The term "operably linked," when applied to DNA sequences, e.g., in an expression vector, indicates that the sequences are arranged so that they function cooperatively in order to achieve their intended purposes, i.e., a promoter sequence allows for initiation of transcription that proceeds through a linked coding sequence as far as the termination signal.

The term "nucleic acid molecule" and "nucleotide sequence," as used herein, refers to a single or double stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate and O-phosphoserine. Amino acid analogs and derivatives can refer to compounds that have the same basic chemical structure as a naturally occurring amino acid, i.e., a carbon that is bound to a hydrogen, a carboxyl group, an amino group and an R group, e.g., homoserine, norleucine, methionine sulfoxide and methionine methyl sulfonium. Such analogs can have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that functions in a manner similar to a naturally occurring amino acid.

As used herein, the term "protein hydrolysates" refers to protein breakdown products, e.g., from protein hydrolysis. Proteins hydrolysates can be prepared by enzymatic, acidic, or alkali hydrolysis of a protein. Protein hydrolysates can include peptides, particularly short chain peptides and peptones, and the constituent amino acids of the protein. Protein hydrolysates can also include fats, for example, free fatty acids, and other meat breakdown products (i.e., products of animal origin).

The terms "isolated" or "purified," used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

As used herein, the term "recombinant" can be used to describe a nucleic acid molecule and refers to a polynucleotide of genomic, RNA, DNA, cDNA, viral, semisynthetic or synthetic origin which, by virtue of its origin or manipulation is not associated with all or a portion of polynucleotide with which it is associated in nature.

The term "fusion," as used herein, refers to joining of different peptide or protein segments by genetic or chemical methods wherein the joined ends of peptide or protein segments may be directly adjacent to each other or may be separated by linker or spacer moieties such as amino acid residues or other linking groups.

2. GPR92 Receptors

The presently disclosed subject matter provides a GPR92 receptor for use in the disclosed methods. The GPR92 receptor of the present disclosure can be a mammalian receptor such as, but not limited to, a feline, canine or human receptor.

In certain embodiments, the GPR92 receptor for use in the presently disclosed subject matter encompasses feline GPR92 having the nucleotide sequence set forth in SEQ ID NO: 1 and/or the amino acid sequence set forth in SEQ ID NO: 4, including fragments thereof (e.g., functional fragments thereof) and variants thereof.

In certain embodiments, the GPR92 receptor for use in the presently disclosed subject matter encompasses canine GPR92 having the nucleotide sequence set forth in SEQ ID NO: 2 and/or the amino acid sequence set forth in SEQ ID NO: 5, including fragments thereof (e.g., functional fragments thereof) and variants thereof.

In certain embodiments, the GPR92 receptor for use in the presently disclosed subject matter encompasses human GPR92 having the nucleotide sequence set forth in SEQ ID NO: 3 and/or the amino acid sequence set forth in SEQ ID NO: 6, including fragments thereof (e.g., functional fragments thereof) and variants thereof.

In certain embodiments, the GPR92 receptor for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2, or 3.

In certain embodiments, the GPR92 receptor for use in the presently disclosed subject matter can include a receptor comprising an amino acid sequence having at least 85%, at least 90%, at least 91%, at least 92%, at least 93%, at least 94%, at least 95%, at least 96%, at least 97%, at least 98% or at least 99% identity to SEQ ID NO: 4, 5 or 6.

The percent identity of two amino acid sequences or of two nucleotide sequences can be determined by aligning the sequences for optimal comparison purposes (e.g., gaps can be introduced in the first sequence for best alignment with the sequence) and comparing the amino acid residues or nucleotides at corresponding positions. The percent identity can be determined by the number of identical amino acid residues or nucleotides in the sequences being compared (e.g., % identity=number of identical positions/total number of positions ×100).

The determination of percent identity between two sequences can be determined using a mathematical algorithm known to those of skill in the art. A non-limiting example of a mathematical algorithm for comparing two sequences is the algorithm of Karlin and Altschul (1990) Proc. Natl. Acad. Sci. USA 87:2264 2268, modified as in Karlin and Altschul (1993) Proc. Natl. Acad. Sci. USA 90:5873 5877, the disclosures of which are incorporated herein by reference in their entireties. The NBLAST and XBLAST programs of Altschul, et al. (1990) J. Mol. Biol. 215:403 410 have incorporated such an algorithm. BLAST nucleotide searches can be performed with the NBLAST program, score=100, wordlength=12, to obtain nucleotide sequences homologous to nucleotide sequences of the invention. BLAST protein searches can be performed with the XBLAST program, score=50, wordlength=3 to obtain amino acid sequences homologous to amino acid sequence of the invention. To obtain gapped alignments for comparison purposes, Gapped BLAST can be utilized as described in Altschul et al. (1997) Nucleic Acids Res. 25:3389 3402, the disclosure of which is incorporated herein by reference in its entirety. Alternatively, PSI Blast can be used to perform an iterated search, which detects distant relationships between molecules. When utilizing BLAST, Gapped BLAST, and PSI Blast programs, the default parameters of the respective programs (e.g., XBLAST and NBLAST) can be used. See http://www.ncbi.nlm.nih.gov. An additional non-limiting example of a mathematical algorithm utilized for the comparison of sequences is the algorithm of Myers and Miller, CABIOS (1989), the disclosure of which is incorporated herein by reference in its entirety. The ALIGN program (version 2.0), which is part of the CGC sequence alignment software package, has incorporated such an algorithm. Other non-limiting examples of algorithms for sequence analysis known in the art include ADVANCE and ADAM as described in Torellis and Robotti (1994) Comput. Appl. Biosci., 10:3 5; and FASTA described in Pearson and Lipman (1988) Proc. Natl. Acad. Sci. 85:2444 8, the disclosures of which are incorporated herein by reference in their entireties. Within FASTA, ktup is a control option that sets the sensitivity and speed of the search.

In certain embodiments, the disclosed subject matter provides for the use of an isolated or purified GPR92 receptor and/or variants and fragments thereof. The disclosed subject matter also encompasses the use of sequence variants. In certain embodiments, variation can occur in either or both the coding and non-coding regions of a nucleotide sequence of GPR92. Variants can include a substantially homologous protein encoded by the same genetic locus in an organism, i.e., an allelic variant. Variants also encompass proteins derived from other genetic loci in an organism, e.g., feline, but having substantial homology to GPR92, i.e., a homolog. Variants can also include proteins substantially homologous to the GPR92 but derived from another organism, i.e., an ortholog. Variants also include proteins that are substantially homologous to GPR92 that are produced by chemical synthesis. Variants also include proteins that are substantially homologous to GPR92 that are produced by recombinant methods.

Orthologs, homologs and allelic variants can be identified using methods well known in the art. These variants can include a nucleotide sequence encoding a receptor that is at least about 60-65%, about 65-70%, about 70-75, about 80-85%, about 90-95%, about 95-99% or more homologous to the nucleotide sequence shown in SEQ ID NO: 1, 2, or 3, or fragments thereof. Such nucleic acid molecules can readily be identified as being able to hybridize under stringent conditions, to the nucleotide sequence shown in SEQ ID NO: 1, 2, or 3, or a fragment thereof. In certain embodiments, two polypeptides (or regions thereof) are substantially homologous when the amino acid sequences are at least about 60-65%, about 65-70%, about 70-75, about 80-85%, about 90-95%, about 95-99% or more homologous to the amino acid sequences shown in SEQ ID NO: 4, 5 or 6, or a fragment thereof. A substantially homologous amino acid sequence, according to the disclosed subject matter, will be encoded by a nucleic acid sequence hybridizing to the nucleic acid sequence, or portion thereof, of the nucleotide sequence shown in SEQ ID NOs: 1, 2, or 3 under stringent conditions.

The GPR92 receptor for use in the methods of the disclosed subject matter can have additions, deletions or substitutions of amino acid residues (variants) which do not substantially alter the biological activity of the receptor. Those individual sites or regions of the receptors which may be altered without affecting biological activity can be determined, for example, by examination of the structure of the receptor extracellular domain. Alternatively and/or additionally, one can empirically determine those regions of the receptor which would tolerate amino acid substitutions by alanine scanning mutagenesis (Cunningham et al., Science 244, 1081-1085 (1989), the disclosure of which is hereby incorporated by reference in its entirety). In the alanine scanning mutagenesis method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the disclosed subject matter encompasses one or more conservative amino acid changes within GPR92. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within GPR92 can be replaced with other amino acid residues from the same side chain family and the altered protein can be tested for retained function using the functional assays described herein. Modifications can be introduced into the GPR92 of the present disclosure by standard techniques known in the art, such as site-directed mutagenesis and PCR-mediated mutagenesis. If such substitutions result in a retention in biological activity, then more substantial changes can be introduced and/or other additions/deletions may be made and the resulting products screened. In certain embodiments, deletions or additions can be from 5-10 residues, alternatively from 2-5 amino acid residues or from 1-2 residues.

The disclosed subject matter also provides for fusion proteins that comprise GPR92, or fragment thereof. In certain embodiments, the disclosed subject matter provides for fusion proteins of GPR92, or functional fragments thereof, and an immunoglobulin heavy chain constant region. In certain embodiments, a fusion protein of the present disclosure can include a detectable marker, a functional group such as a carrier, a label, a stabilizing sequence or a mechanism by which GPR92 agonist binding can be detected. Non-limiting embodiments of a label include a FLAG tag, a His tag, a MYC tag, a maltose binding protein and others known in the art. The presently disclosed subject matter also provides nucleic acids encoding such fusion proteins, vectors containing fusion protein-encoding nucleic acids and host cells comprising such nucleic acids or vectors. In certain embodiments, fusions can be made at the amino terminus (N-terminus) of GPR92 or at the carboxy terminus (C-terminus) of GPR92.

In certain embodiments, GPR92 as disclosed herein can contain additional amino acids at the N-terminus and/or at the C-terminus end of the sequences, e.g., when used in the methods of the disclosed subject matter. In certain embodiments, the additional amino acids can assist with immobilizing the polypeptide for screening purposes, or allow the polypeptide to be part of a fusion protein, as disclosed above, for ease of detection of biological activity.

3. Methods for Identifying GPR92 Modulating Compounds

The present disclosure further provides methods for identifying compounds that modulate the activity and/or expression of a GPR92 receptor. For example, and not by way of limitation, the modulator can be an agonist or an antagonist. The presently disclosed subject matter provides in silico and in vitro methods for identifying compounds that modulate the activity and/or expression of a GPR92 receptor, disclosed above.

3.1 in Silico Methods

The presently disclosed subject matter further provides in silico methods for identifying compounds that can potentially interact with a GPR92 receptor and/or modulate the activity and/or expression of a GPR92 receptor.

In certain embodiments, the method can include predicting the three-dimensional structure (3D) of GPR92 and screening the predicted 3D structure with putative GPR92 modulating compounds (i.e., test compounds). The method can further include predicting whether the putative compound would interact with the binding site of the receptor by analyzing the potential interactions with the putative compound and the amino acids of the receptor. The method can further include identifying a test compound that can bind to and/or modulate the biological activity of GPR92 by determining whether the 3D structure of the compound fits within the binding site of the 3D structure of the receptor.

In certain embodiments, GPR92 for use in the disclosed method can have the amino acid sequence of SEQ ID NO: 4, 5 or 6, or a fragment or variant thereof. In certain embodiments, GPR92 for use in the presently disclosed subject matter can include a receptor comprising an amino acid sequence having at least 85%, at least 90%, at least 91%, at least 92%, at least 93%, at least 94%, at least 95%, at least 96%, at least 97%, at least 98% or at least 99% identity to SEQ ID NO: 4, 5 or 6, or a fragment or variant thereof. In certain embodiments, GPR92 for use in the disclosed method can have the nucleotide sequence of SEQ ID NO: 1, 2 or 3, or a fragment or variant thereof. In certain embodiments, GPR92 for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2 or 3, or a fragment or variant thereof.

Non-limiting examples of compounds (e.g., potential GPR92 modulators) that can be tested using the disclosed methods include any small chemical compound, or any biological entity, such as peptides, salts, and amino acids known in the art. In certain embodiments, the test compound can be a small chemical molecule. In certain embodiments, the test compound can be a protein hydrolysate. In certain embodiments, the test compound can be a known GPR92 agonist, for example, but not limited to, NAG (N-Arachidonylglycine), FPP (3,7,11-Trimethyl-2,6,10-dodecatrien-1-yl pyrophosphate), LPA (18:0) (1-stearoyl-2-hydroxy-sn-glycero-3-phosphate), CPA (18:1) (1-oleoyl-sn-glycero-2,3-cyclic-phosphate), LPA (14:0) (1-myristoyl-2-hydroxy-sn-glycero-3-phosphate), LPA (16:0) (1-palmitoyl-2-hydroxy-sn-glycero-3-phosphate), and LPA (18:1) (1-oleoyl-2-hydroxy-sn-glycero-3-phosphate). In certain embodiments, the test compound can be farnesyl monophosphate (FMP), alkyl-glycerophosphate (AGP, also known as alkyl-LPA), cyclic phosphatidic acid (CPA); carba-CPA (CCPA), 2-carba-CPA (2CCPA), or 3-carba-CPA (3CCPA). In certain embodiments, the test compound can be any GPR92 agonists disclosed in Williams, et al., The Journal of Biological Chemistry VOL. 284, NO. 25, pp. 17304-17319, Jun. 19, 2009.

In certain embodiments, structural models of a GPR92 receptor can be built using crystal structures of other GPCRs as templates for homology modeling. For example, and not by way of limitation, structural models can be generated using the crystal structures of other Class A GPCRs. In certain embodiments, a structural model of GPR92 can be based on a known or a combination of known crystal structures of Class A GPCRs. (See, e.g., Lee et al., Eur. J Pharmacol. 2015 May 14. pii: S0014-2999 (15) 30012-1, and Berman et al., Nucleic Acids Research, 28: 235-242 (2000), each of which is incorporated by reference in its entirety herein). Examples of crystal structures of other Class A GPCRs include 4N6H of the Human Delta Opioid receptor; and/or 4MBS of the CCR5 Chemokine Receptor; and/or 4PHU of the human GPR40. FIGS. 11-18 depict structural models of GPR92 that can be used in the disclosed in silico methods. Any suitable modeling software known in the art can be used. In certain embodiments, the Modeller software package (Eswar et al., Curr Protoc Bioinformatics, John Wiley & Sons, Inc., Supplement 15, 5.6.1-5.6.30 (2006)) and/or the I-TASSER suite of programs (Yang et al., Nature Methods, 12: 7-8 (2015) can be used to generate the three-dimensional protein structure.

In certain embodiments, the in silico methods of identifying a compound that binds to GPR92 comprises determining whether a test compound interacts with one or more amino acids of a GPR92 interacting domain, as described herein.

Compounds that are identified by the disclosed in silico methods can be further tested using the in vitro methods disclosed herein.

3.2 GPR92 Receptor Binding Site

The present application provides for methods of screening for compounds that modulate the activity of a GPR92 receptor, for example, feline, canine or human GPR92, wherein the compounds interact with one or more amino acids of the receptor. In certain embodiments, the binding site of a GPR92 receptor comprises amino acids within the 7 Transmembrane (7TM) domain of the receptor, and can be identified by generating an interaction map of the receptor using in silico modeling, as described herein. In one non-limiting example, the presence of an amino acid in the 7TM interaction map means that the residue is in the vicinity of the ligand binding environment, and interacts with the ligand.

In certain embodiments, the interaction between a compound and one or more amino acids of the GPR92 receptor described herein can comprise one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into a feline or canine GPR92 binding pocket as described herein, for example, using molecular docking, molecular modeling, molecular simulation, or other means known to persons of ordinary skill in the art.

In certain embodiments, the interaction is a salt bridge interaction.

In certain embodiments, the interaction is a hydrogen bond interaction.

In certain embodiments, the interaction is a hydrophobic interaction.

In certain embodiments, the compounds identified according to the methods described herein that modulate the activity of a GPR92 receptor interact with one or more amino acids in in a transmembrane domain of the GPR92 receptor, for example, a 7 Transmembrane (7TM) domain. In certain embodiments, the compounds interact with one or more amino acids in a GPR92 active site comprising a hydrophobic region located between the helices.

In certain embodiments, the amino acids that the compounds interact with comprise 1, 2, 3, 4, 5, 6, 7, 8, 9, 10, 11, 12, 13, 14, 15, 16, 17, 18, 19 or more of Arg83 on Helix 2;

Gly103, Phe106, Gln107, Met110, and/or Cys114 on Helix 3; Thr161 and/or His165 on Helix 4; Ala200, Gly204, and/or Pro208 on Helix 5; Phe248, Phe252, Tyr255, Asn256, and/or Leu259 on Helix 6; Arg281, Met285, and/or Val288 on Helix 7; and/or Glu182 on the second extracellular (EC2) loop of a GPR92 receptor, for example, a feline GPR92 receptor, for example, as described by SEQ ID NO: 4.

In certain embodiments, the amino acids that the compounds interact with comprise one or more of Arg83, Arg281, Tyr255, and combinations thereof, of a GPR92 receptor, for example, a feline GPR92 receptor, for example, as described by SEQ ID NO: 4. In certain embodiments, the compounds further interact with one or more amino acids selected from Gly103, Phe106, Gln107, Met110, and/or Cys114 on Helix 3; Thr161 and/or His165 on Helix 4; Ala200, Gly204, and/or Pro208 on Helix 5; Phe248, Phe252, Asn256, and/or Leu259 on Helix 6; Met285, and/or Val288 on Helix 7; and/or Glu182 on the second extracellular (EC2) loop, and combinations thereof, of a GPR92 receptor, for example, a feline GPR92 receptor, for example, as described by SEQ ID NO: 4.

In certain embodiments, the amino acids that the compounds interact with comprise 1, 2, 3, 4, 5, 6, 7, 8, 9, 10, 11, 12, 13, 14, 15, 16, 17, 18, 19 or more of Arg76 on Helix 2; Gly96, Phe99, Gln100, Met103, and/or Cys107 on Helix 3; Thr154 and/or His158 on Helix 4 (His158 is at the end of Helix 4); Ala193, Gly197, and/or Pro201 on Helix 5; Phe241, Phe245, Tyr248, Asn249, and/or Leu252 on Helix 6; Arg274, Met278, and/or Val281 on Helix 7; and/or Glu175 on the EC2 loop of a GPR92 receptor, for example, a canine GPR92, for example, as described by SEQ ID NO: 5.

In certain embodiments, the amino acids that the compounds interact with comprise one or more of Arg76, Arg274, Tyr248, and combinations thereof, of a GPR92 receptor, for example, a canine GPR92 receptor, for example, as described by SEQ ID NO: 5. In certain embodiments, the compounds further interact with one or more amino acids selected from Gly96, Phe99, Gln100, Met103, and/or Cys107 on Helix 3; Thr154 and/or His158 on Helix 4 (His158 is at the end of Helix 4); Ala193, Gly197, and/or Pro201 on Helix 5; Phe241, Phe245, Asn249, and/or Leu252 on Helix 6; Met278, and/or Val281 on Helix 7; and/or Glu175 on the EC2 loop, and combinations thereof, of a GPR92 receptor, for example, a canine GPR92, for example, as described by SEQ ID NO: 5.

In certain embodiments, the compounds bind to amino acid residues in a GPR92 receptor that are homologous to those described herein, for example, in a GPR92 of a species other than a feline or canine, or from a feline or canine expressing a variant of the GPR92 amino acid and/or nucleic acid sequences described herein.

3.3 In Vitro Methods

The presently disclosed subject matter further provides in vitro methods for identifying compounds that can modulate the activity and/or expression of a GPR92 receptor.

The GPR92 receptor for use in the presently disclosed methods can include isolated or recombinant GPR92 or cells expressing GPR92, disclosed herein. In certain embodiments, the GPR92 receptor for use in the disclosed methods can have the amino acid sequence of SEQ ID NO: 4, 5 or 6, or a fragment or variant thereof. In certain embodiments, the GPR92 for use in the disclosed method can have at least 85%, at least 90%, at least 91%, at least 92%, at least 93%, at least 94%, at least 95%, at least 96%, at least 97%, at least 98% or at least 99% identity to the amino acid sequence of SEQ ID NO: 4, 5 or 6, or a fragment or variant thereof. In certain embodiments, the GPR92 receptor for use in the disclosed method can have the nucleotide sequence of SEQ ID NO: 1, 2 or 3, or a fragment or variant thereof. In certain embodiments, the GPR92 receptor for use in the presently disclosed subject matter can include a receptor comprising a nucleotide sequence having at least 85%, at least 90%, at least 91%, at least 92%, at least 93%, at least 94%, at least 95%, at least 96%, at least 97%, at least 98% or at least 99% identity to SEQ ID NO: 1, 2 or 3, or a fragment or variant thereof.

In certain embodiments, the method for identifying compounds that modulate the activity and/or expression of a GPR92 receptor comprises measuring the biological activity of GPR92 in the absence and/or presence of a test compound. In certain embodiments, the method can include measuring the biological activity of GPR92 in the presence of varying concentrations of the test compound. The method can further include identifying the test compounds that result in a modulation of the activity and/or expression of the GPR92 receptor compared to the activity and/or expression of the GPR92 receptor in the absence of the test compound.

In certain embodiments, the compounds identified according to the methods described herein increase the biological activity of a GPR92 receptor by at least about 5%, 10%, 15%, 20%, 25%, 30%, 35%, 40%, 45%, 50%, 55%, 60%, 65%, 70%, 75%, 80%, 85%, 90%, 95%, 100%, or more, compared to the biological activity of the GPR92 receptor when the compound is not present.

In certain embodiments, the method can further include analyzing two or more, three or more or four or more test compounds in combination. In certain embodiments, the two or more, three or more or four or more test compounds can be from different classes of compounds, e.g., amino acids, small chemical compounds, and/or protein hydrolysates. For example, and not by way of limitation, the method can include analyzing the effect of one or more small chemical test compounds on the biological activity and/or expression of GPR92 in the presence of one or more amino acid test compounds. In certain embodiments, the method for identifying compounds that modulate the activity and/or expression of a GPR92 receptor comprises analyzing the effect of a test compound on the biological activity and/or expression of GPR92 in the presence of a GPR92 agonist, e.g., NAG (N-Arachidonylglycine), FPP (3,7,11-Trimethyl-2,6,10-dodecatrien-1-yl pyrophosphate), LPA (18:0) (1-stearoyl-2-hydroxy-sn-glycero-3-phosphate), CPA (18:1) (1-oleoyl-sn-glycero-2,3-cyclic-phosphate), LPA (14:0) (1-myristoyl-2-hydroxy-sn-glycero-3-phosphate), LPA (16:0) (1-palmitoyl-2-hydroxy-sn-glycero-3-phosphate), and LPA (18:1) (1-oleoyl-2-hydroxy-sn-glycero-3-phosphate). In certain embodiments, the test compound can be farnesyl monophosphate (FMP), alkyl-glycerophosphate (AGP, also known as alkyl-LPA), cyclic phosphatidic acid (CPA); carba-CPA (CCPA), 2-carba-CPA (2CCPA), or 3-carba-CPA (3CCPA). In certain embodiments, the test compound can be any GPR92 agonists disclosed in Williams, et al., The Journal of Biological Chemistry VOL. 284, NO. 25, pp. 17304-17319, Jun. 19, 2009.

In certain embodiments, the method for identifying compounds that modulate the activity and/or expression of a GPR92 receptor comprises determining whether a compound modulates the receptor directly, for example, as an agonist or antagonist. In certain embodiments, the method comprises determining whether a compound indirectly modulates the activity of the receptor (e.g., as an allosteric modulator), for example, by enhancing or decreasing the effect of other compounds on activating or inhibiting receptor activity.

In certain embodiments, the method for identifying compounds that modulate the activity and/or expression of a GPR92 receptor comprises expressing a GPR92 receptor in a cell line and measuring the biological activity of the receptor in the presence and/or absence of a test compound. The method can further comprise identifying test compounds that modulate the activity of the receptor by determining if there is a difference in receptor activation in the presence of a test compound compared to the activity of the receptor in the absence of the test compound. In certain embodiments, the selectivity of the putative GPR92 modulator can be evaluated by comparing its effects on other GPCRs or taste receptors, e.g., umami, fatty acid, T1R, CaSR, etc. receptors.

Activation of the receptor in the disclosed methods can be detected through the use of a labeling compound and/or agent. In certain embodiments, the activity of a GPR92 receptor can be determined by the detection of secondary messengers such as, but not limited to, cAMP, cGMP, IP3, DAG or calcium. In certain embodiments, the activity of the receptor can be determined by the detection of the intracellular calcium levels. Monitoring can be by way of luminescence or fluorescence detection, such as by a calcium sensitive fluorescent dye. In certain embodiments, the intracellular calcium levels can be determined using a cellular dye, e.g., a fluorescent calcium indicator such as Calcium 4. In certain non-limiting embodiments, the calcium sensitive fluorescent dye is selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof. In certain embodiments, the intracellular calcium levels can be determined by measuring the level of calcium binding to a calcium-binding protein, for example, calmodulin. Alternatively, and/or additionally, activity of the GPR92 receptor can be determined by detection of the phosphorylation, transcript levels and/or protein levels of one or more downstream protein targets of the GPR92 receptor.

The cell line used in the disclosed methods can include any cell type that is capable of expressing GPR92. Non-limiting examples of cells that can be used in the disclosed methods include HeLa cells, Chinese hamster ovary cells (CHO cells), African green monkey kidney cells (COS cells), Xenopus oocytes, HEK-293 cells and murine 3T3 fibroblasts. In certain embodiments, the method can include expressing GPR92 in HEK-293 cells. In certain embodiments, the method can include expressing GPR92 in COS cells. In certain embodiments, the cells constitutively express GPR92. In another embodiment, expression of GPR92 by the cells is inducible.

In certain embodiments, the cell expresses a calcium-binding photoprotein, wherein the photoprotein luminesces upon binding calcium. In certain embodiments, the calcium binding photoprotein comprises the protein clytin. In certain embodiments the clytin is a recombinant clytin. In certain embodiments, the clytin comprises an isolated clytin, for example, a clytin isolated from *Clytia gregarium*. In certain embodiments, the calcium-binding photoprotein comprises the protein aequorin, for example, a recombinant aequorin or an isolated aequorin, such as an aequorin isolated from *Aequorea victoria*. In certain embodiments, the calcium-binding photoprotein comprises the protein obelin, for example, a recombinant obelin or an isolated obelin, such as an obelin isolated from *Obelia longissima*.

In certain embodiments, expression of GPR92 in a cell can be performed by introducing a nucleic acid encoding GPR92 into the cell. For example, and not by way of limitation, a nucleic acid having the nucleotide sequence set forth in SEQ ID NO: 1, 2 or 3, or a fragment thereof, can be introduced into a cell. In certain embodiments, the introduction of a nucleic acid into a cell can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 (1985), the disclosures of which are hereby incorporated by reference in their entireties) and can be used in accordance with the disclosed subject matter. In certain embodiments, the technique can provide for stable transfer of nucleic acid to the cell, so that the nucleic acid is expressible by the cell and inheritable and expressible by its progeny. In certain embodiments, the technique can provide for a transient transfer of the nucleic acid to the cell, so that the nucleic acid is expressible by the cell, wherein heritability and expressibility decrease in subsequent generations of the cell's progeny.

In certain embodiments, the nucleic acid encoding a GPR92 receptor is comprised in a cloning vector, for example, a pcDNA3.1 vector or a pcDNA5 TO vector, that is introduced into the cell.

In certain embodiments, the method can include identifying compounds that bind to GPR92. The method can comprise contacting a GPR92 receptor with a test compound and measuring binding between the compound and the GPR92 receptor. For example, and not by way of limitation, the methods can include providing an isolated or purified GPR92 receptor in a cell-free system, and contacting the receptor with a test compound in the cell-free system to determine if the test compound binds to the GPR92 receptor. In certain embodiments, the method can comprise contacting a GPR92 receptor expressed on the surface of a cell with a candidate compound and detecting binding of the candidate compound to the GPR92 receptor. The binding can be measured directly, e.g., by using a labeled test compound, or can be measured indirectly. In certain embodiments, the detection comprises detecting a physiological event in the cell caused by the binding of the compound to the GPR92 receptor, e.g., an increase in the intracellular calcium levels. For example, and not by way of limitation, detection can be performed by way of fluorescence detection, such as a calcium sensitive fluorescent dye, by detection of luminescence, or any other method of detection known in the art. In certain non-limiting embodiments, the calcium sensitive fluorescent dye is selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

In certain non-limiting embodiments, the in vitro assay comprises cells expressing a GPR92 that is native to the cells. Examples of such cells expressing a native GPR92 include, for example but not limited to, dog (canine) and/or cat (feline) taste cells (e.g., primary taste receptor cells). In certain embodiments, the dog and/or cat taste cells expressing GPR92 are isolated from a dog and/or cat and cultured in vitro. In certain embodiments, the taste receptor cells can be immortalized, for example, such that the cells isolated from a dog and/or cat can be propagated in culture.

In certain embodiments, expression of GPR92 in a cell can be induced through gene editing, for example, through use of the CRISPR gene editing system to incorporate a GPR92 gene into the genome of a cell, or to edit or modify a GPR92 gene native to the cell.

In certain embodiments, the in vitro methods of identifying a compound that binds to a GPR92 receptor comprise determining whether a test compound interacts with one or more amino acids of a GPR92 interacting domain, as described herein.

In certain embodiments, compounds identified as modulators of GPR92 can be further tested in other analytical methods including, but not limited to, in vivo assays, to confirm or quantitate their modulating activity.

In certain embodiments, methods described herein can comprise determining whether the GPR92 modulator is a taste enhancing compound, e.g., a GPR92 agonist.

In certain embodiments, the methods of identifying a GPR92 modulator can comprise comparing the effect of a test compound to a GPR92 agonist. For example, a test compound that increases the activity of the receptor compared to the activity of the receptor when contacted with a GPR92 agonist can be selected as a GPR92 modulating compound (e.g., as an agonist).

In certain embodiments, the methods of identifying a GPR92 modulator can comprise determining whether a test compound modulates the activity of the receptor when the receptor is contacted with an agonist, or whether the test compound can modulate the activity of a positive allosteric modulator (PAM). Test compounds that increase or decrease the effect of said agonist or PAM on the receptor can be selected as a GPR92 modulating compound (e.g., as an allosteric modulator).

In certain embodiments, the GPR92 receptor modulators of the present disclosure comprise a salt of the GPR92 modulator, for example, but not limited to, an acetate salt or a formate salt. In certain embodiments, the GPR92 modulator salt comprises an anion (−) (for example, but not limited to, Cl−, Br−, $CO_3^{2-}$, $HCO_3^-$, OH−, $NO_3^-$, $PO_4^{3-}$, $SO_4^{2-}$, $CH_3COO^-$, $HCOO^-$ and $C_2O_4^{2-}$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $NH_4^+$ and $H_3O^+$). In other embodiments, the GPR92 agonist salt comprises a cation (+) bonded via an ionic bond with an anion (−).

In certain embodiments, the GPR92 modulators of the present application are identified through in silico modeling of a GPR92 receptor, e.g., feline, canine, or human GPR92, wherein the GPR92 agonists of the present application comprise a structure that fits within a binding site of the GPR92 receptor. In certain embodiments, the in silico method comprises the in silico methods described above and in the Examples section of the present application.

In certain embodiments, the GPR92 modulators of the present application are identified through an in vitro method, wherein the GPR92 agonist compounds activate and/or modulate a GPR92 receptor, disclosed herein, expressed by cells in vitro. In certain embodiments, the in vitro method comprises the in vitro methods described above and in the Examples section of the present application.

EXAMPLES

The presently disclosed subject matter will be better understood by reference to the following Examples, which are provided as exemplary of the invention, and not by way of limitation.

Example 1—Identification of GPR92 Modulators Using in Silico Assays

The present example describes the computational modeling of feline and canine GPR92 to identify putative modulators of GPR92.

Computational approaches were used to analyze the three-dimensional structure of the GPR92 receptor to identify polypeptide regions that can be exploited to selectively modulate the GPR92 receptor. A structural homology model of the 7 Transmembrane domain of the GPR92 receptor was generated based on the structures of Class A GPCRs from the Protein Data Bank (PDB). (See Berman et al., Nucleic Acids Research, 28: 235-242 (2000), which is incorporated by reference herein in its entirety). The homology models were built using the I-TASSER suite of programs (see Yang et al., Nature Methods, 12: 7-8 (2015), which is incorporated by reference herein in its entirety) and the Modeller software package (see Eswar et al., Curr Protoc Bioinformatics, John Wiley & Sons, Inc., Supplement 15, 5.6.1-5.6.30 (2006), which is incorporated by reference herein in its entirety) from the Discovery Studio (DS) suite of programs from Dassault Systemes (BIOVIA Corp., San Diego, Calif., USA).

Figure 7:
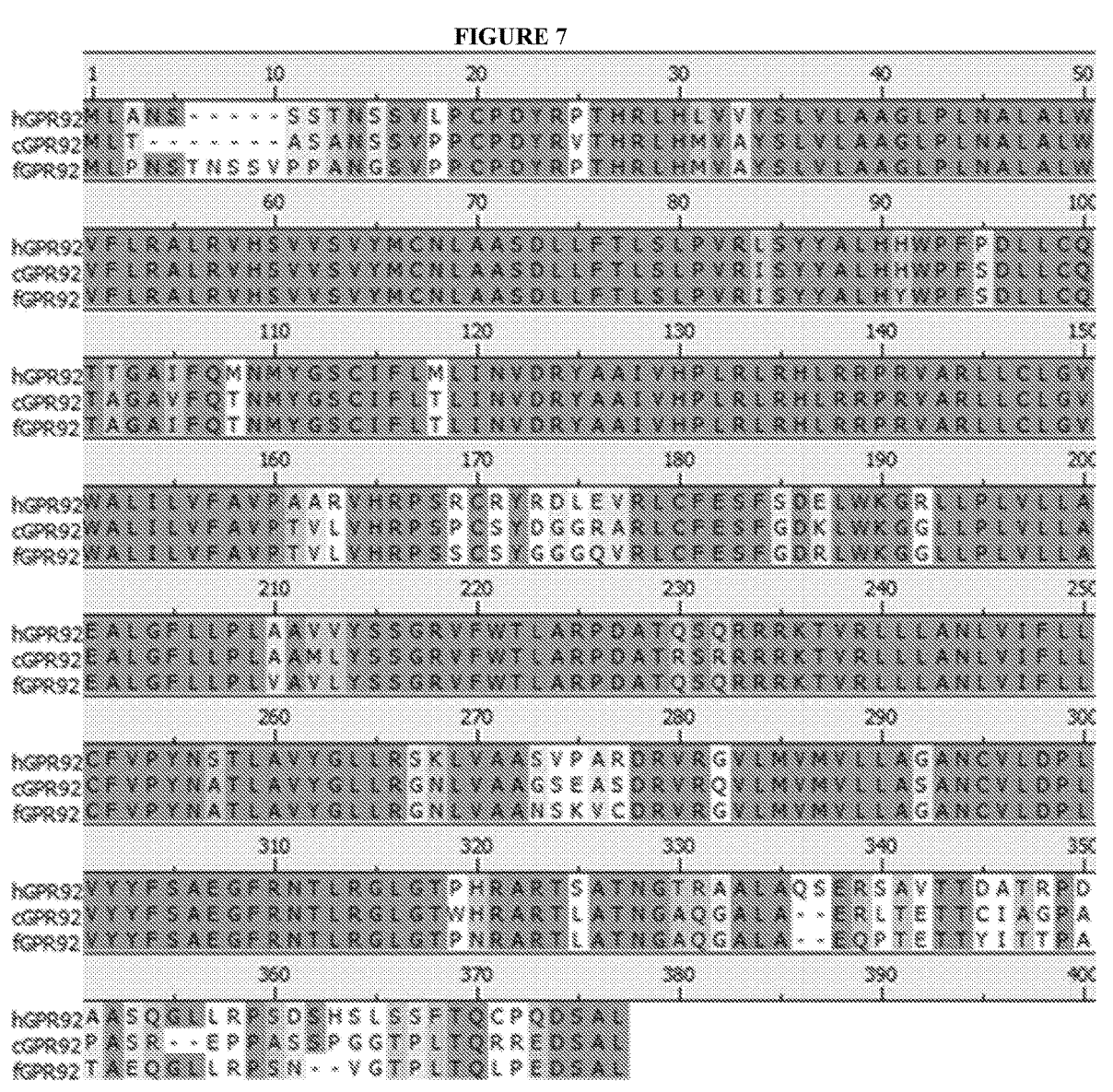
Figure 9:
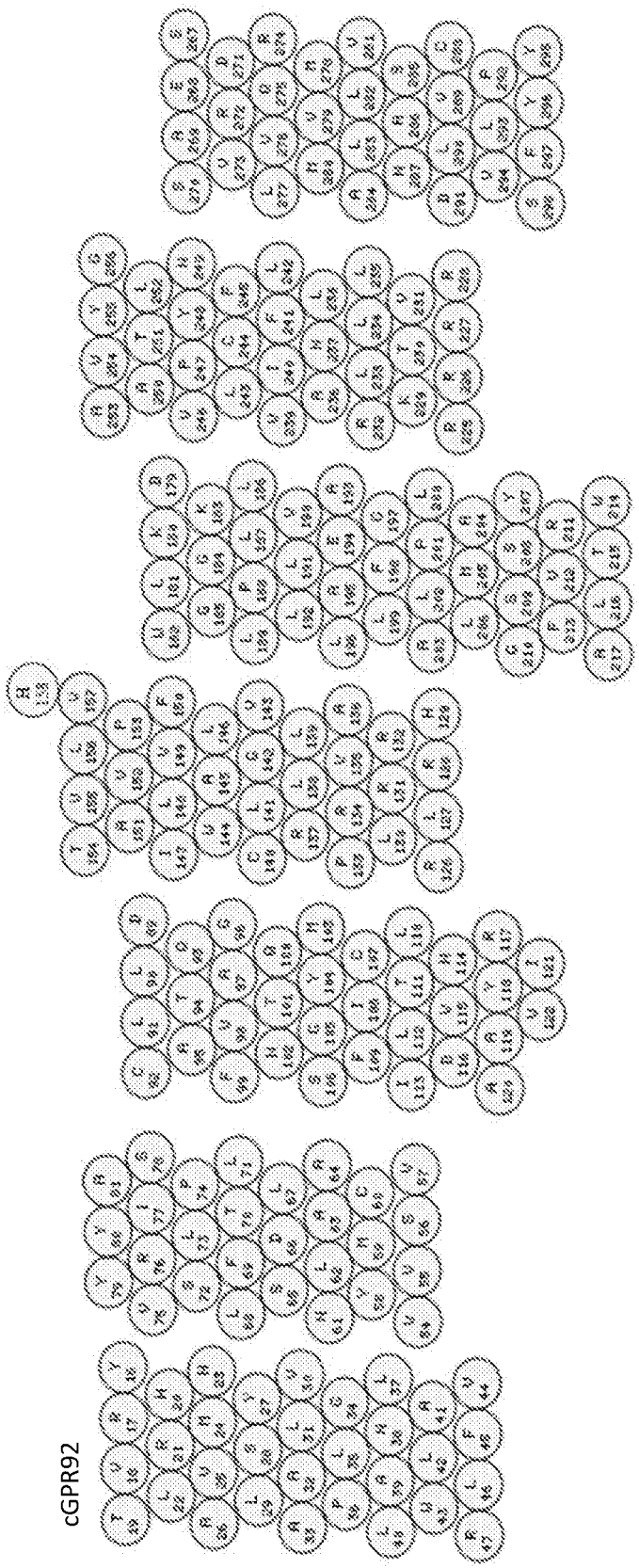
FIG. 9 shows the helix plot of the 7TM domain of canine GPR92.
Figure 10:
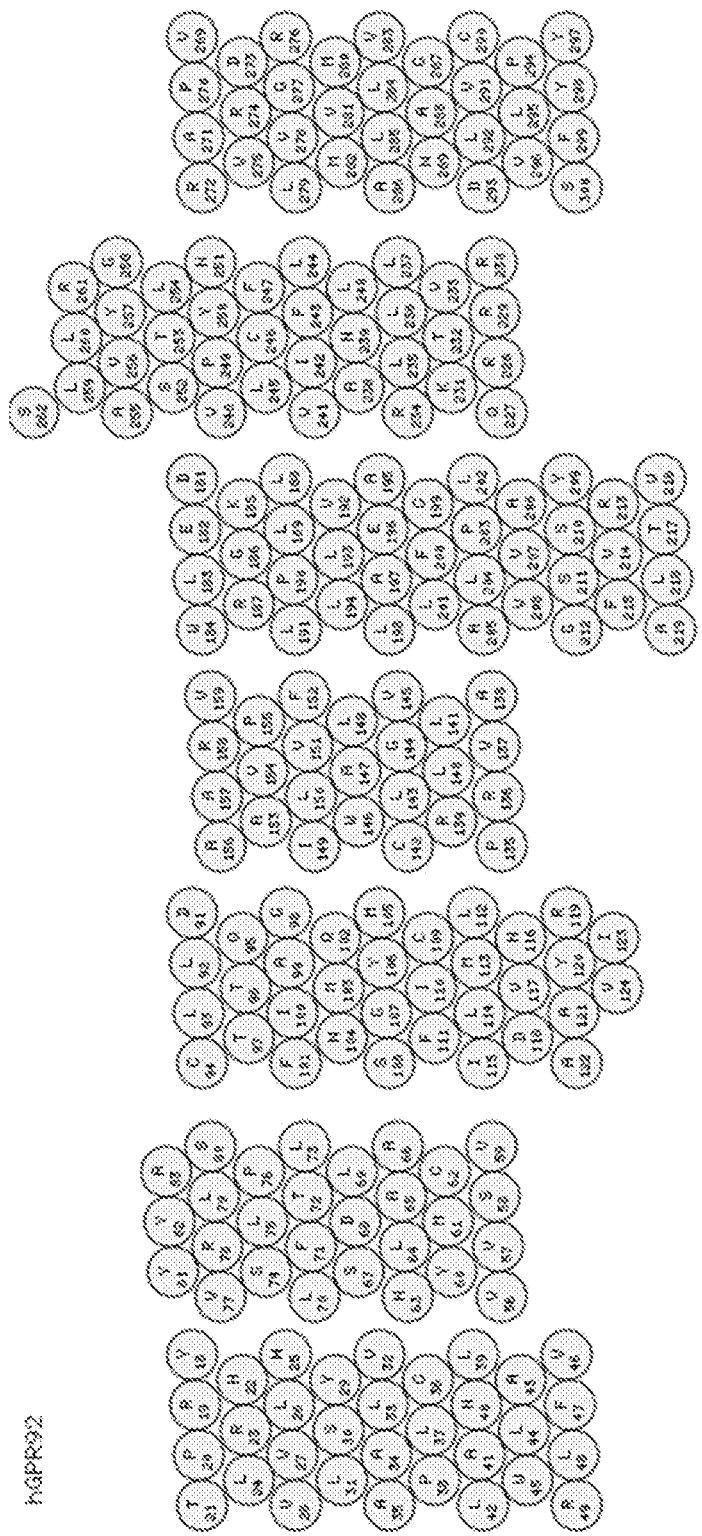
FIG. 10 shows the helix plot of the 7TM domain of human GPR92.

"In silica" modeling was used to identify amino acids in the 7 Transmembrane (7TM) domain of the feline and canine GPR92 receptor that interact with compounds docked in the receptor active site. Class A GPCR receptors include a 7 Transmembrane (7TM) domain. A sequence alignment of the amino acid sequence of the GPR92 receptors from felines (fGPR92), canines (cGPR92), and humans (hGPR92) was performed and showed an overall 77% sequence identity (FIG. 7). The 7TM domain of GPR92 consists of seven transmembrane helices. FIGS. 8-10 provide helix plots showing sequence starts, stops, and extents for each of the seven helices in fGPR92, cGPR92, and hGPR92, respectively.

Residues lining the active site of feline GPR92 include: Arg83 on Helix 2; Gly103, Phe106, Gln107, Met110, and Cys114 on Helix 3; Thr161 and His165 on Helix 4; Ala200, Gly204, and Pro208 on Helix 5; Phe248, Phe252, Tyr255, Asn256, and Leu259 on Helix 6; Arg281, Met285, and Val288 on Helix 7; as well as Glu182 on the second extracellular (EC2) loop. In particular, as described below, Arg83, Arg281, and Tyr255 played critical roles in the homology models by forming salt-bridges and hydrogen-bonding interactions to coordinate the negatively charged head-groups and polar parts of compounds bound to the active site.

Residues lining the active site of canine GPR92 include: Arg76 on Helix 2; Gly96, Phe99, Gln100, Met103, and Cys107 on Helix 3; Thr154 and His158 on Helix 4 (His158 is at the end of Helix 4); Ala193, Gly197, and Pro201 on Helix 5; Phe241, Phe245, Tyr248, Asn249, and Leu252 on Helix 6; Arg274, Met278, and Val281 on Helix 7; as well as Glu175 on the EC2 loop. In particular, as described below, Arg76, Arg274, and Tyr248 played critical roles in the homology models by forming salt-bridges and hydrogen-bonding interactions to coordinate the negatively charged head-groups and polar parts of compounds bound to the active site.

Four known human GPR92 binding compounds were docked into the active site of the 7TM domain of each of feline and canine GPR92. The docking program, BioDock, from BioPredict, Inc. (Oradell, N.J., USA) was used to model the docking of the compounds into the receptor active site.

Figure 11A:
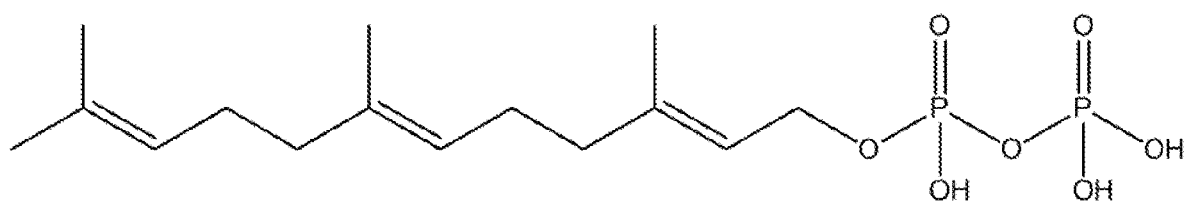
FIG. 11A-C shows the in silico modeling of the binding of compound FPP (3,7,11-Trimethyl-2,6,10-dodecatrien-1-yl pyrophosphate) to the 7TM domain of feline GPR92. (A) Shows the structure of the binding compound, (B) shows a model of the compound binding to GPR92, and (C) shows the putative GPR92 amino acid residues that interact with the binding compound.
Figure 11B:
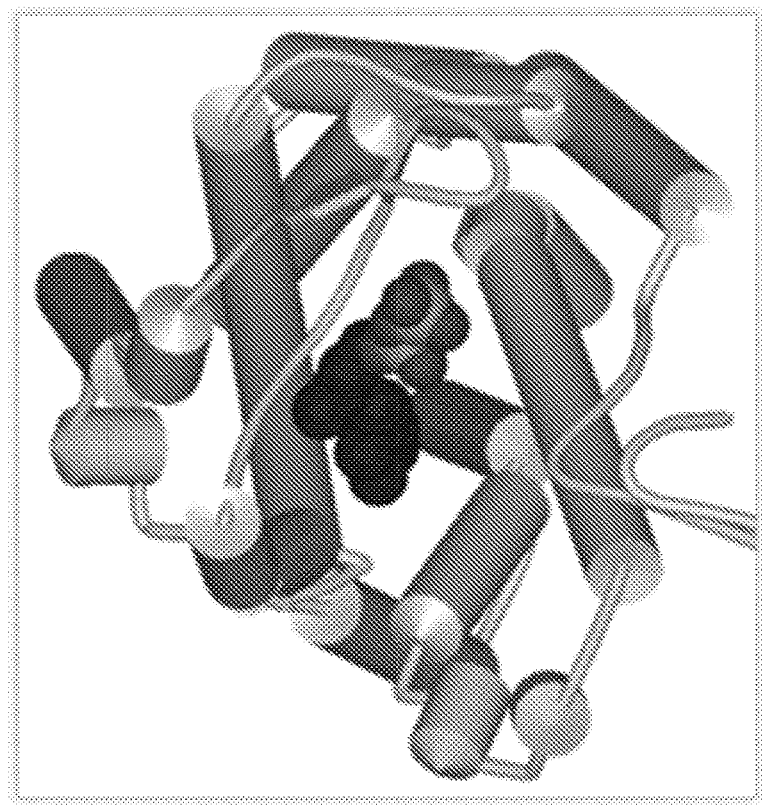
Figure 11C:
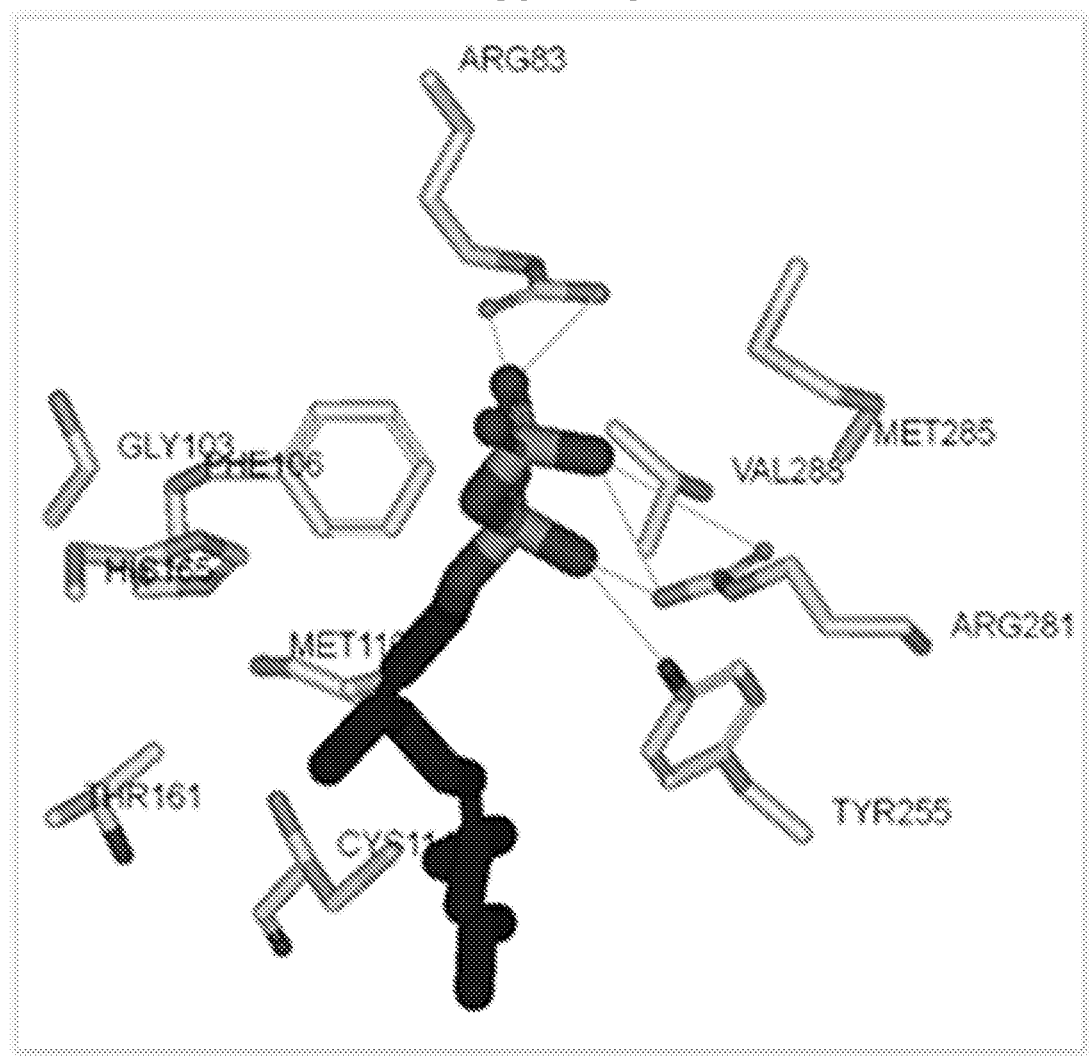
Figure 12A:
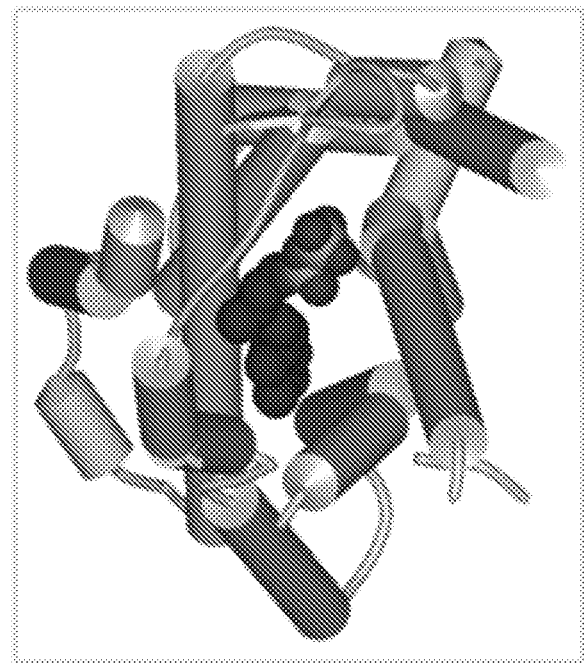
FIG. 12A-B shows the in silico modeling of the binding of compound FPP (3,7,11-Trimethyl-2,6,10-dodecatrien-1-yl pyrophosphate) to the 7TM domain of canine GPR92. (A) Shows a model of the compound binding to GPR92 and (B) shows the putative GPR92 amino acid residues that interact with the binding compound.
Figure 12B:
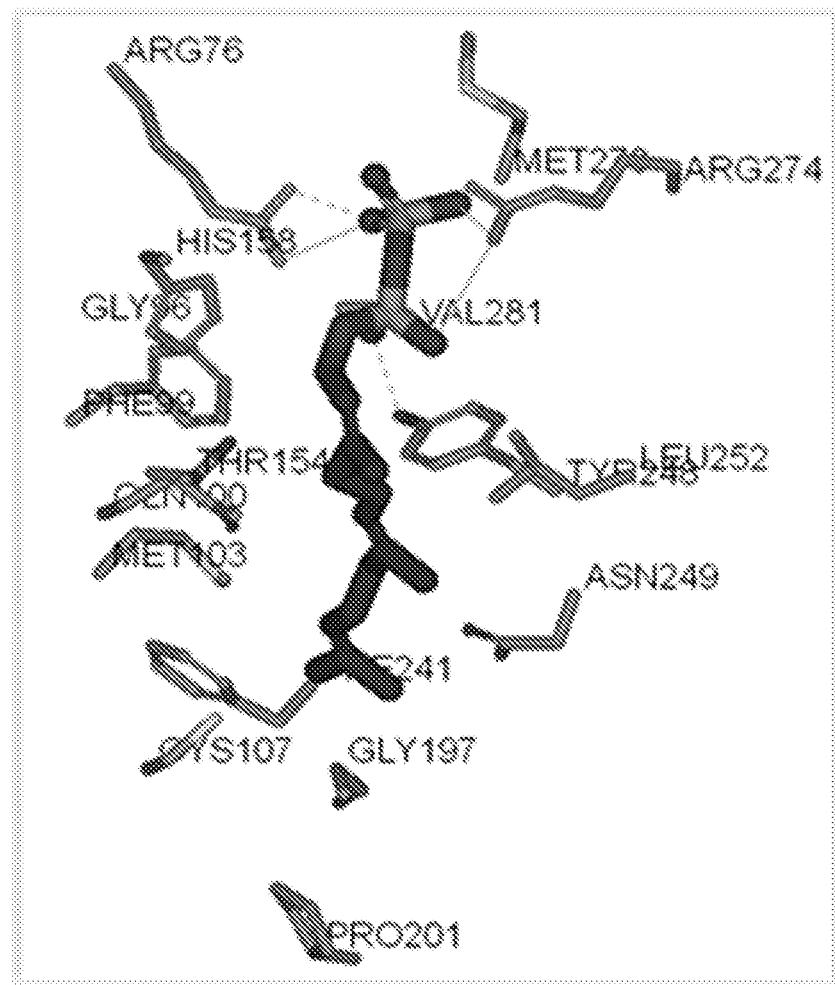

FPP (3,7,11-Trimethyl-2,6,10-dodecatrien-1-yl pyrophosphate) was observed to make potential salt bridge interactions and hydrogen bonds to Arg83 and to Arg281, as well as a hydrogen bond to Tyr255 in feline GPR92 (FIG. 11). Similarly, FPP was observed to make potential salt bridge interactions and hydrogen bonds to Arg76 and to Arg274, as well as a hydrogen bond to Tyr248 in canine GPR92 (FIG. 12). Additionally, the tail of FPP formed an extensive network of hydrophobic contacts with both feline and canine GPR92.

Figure 13A:
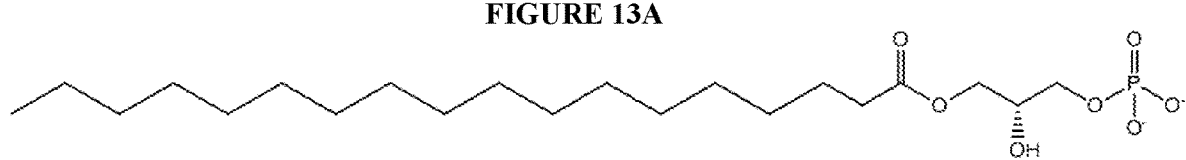
FIG. 13A-C shows the in silico modeling of the binding of compound LPA (18:0) (1-stearoyl-2-hydroxy-sn-glycero-3-phosphate) to the 7TM domain of feline GPR92. (A) Shows the structure of the binding compound, (B) shows a model of the compound binding to GPR92, and (C) shows the putative GPR92 amino acid residues that interact with the binding compound.
Figure 13B:
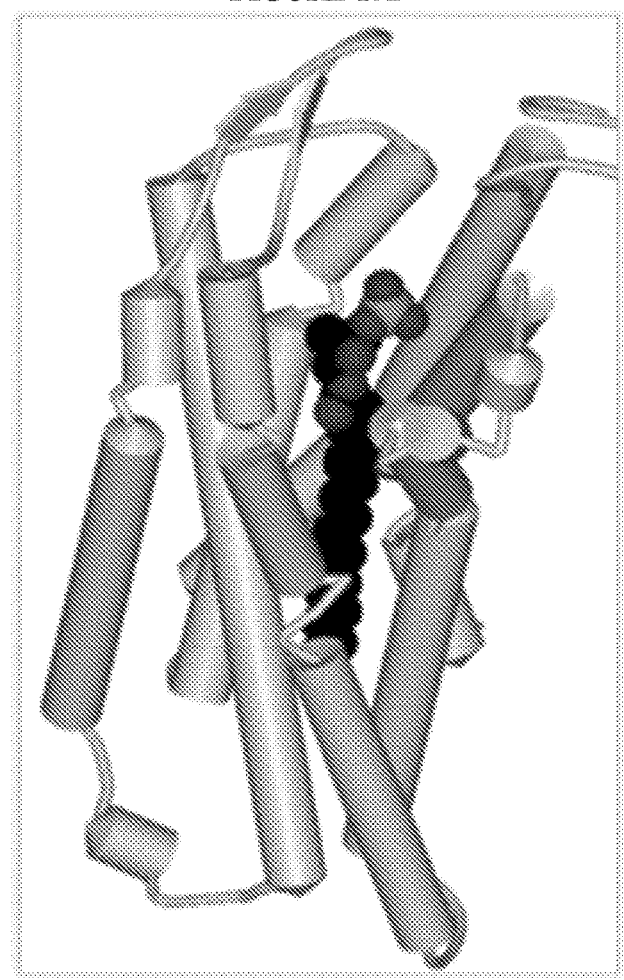
Figure 13C:
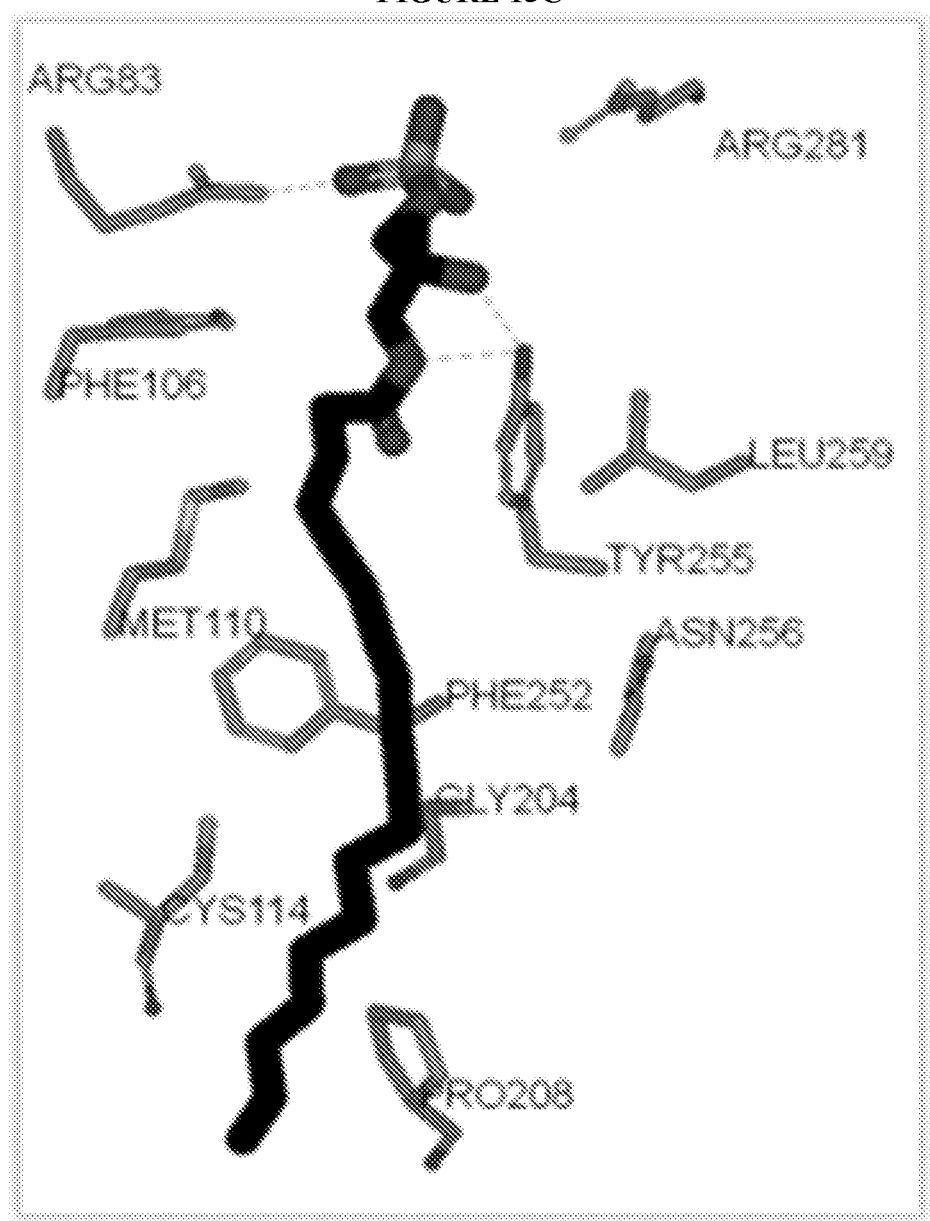
Figure 14A:
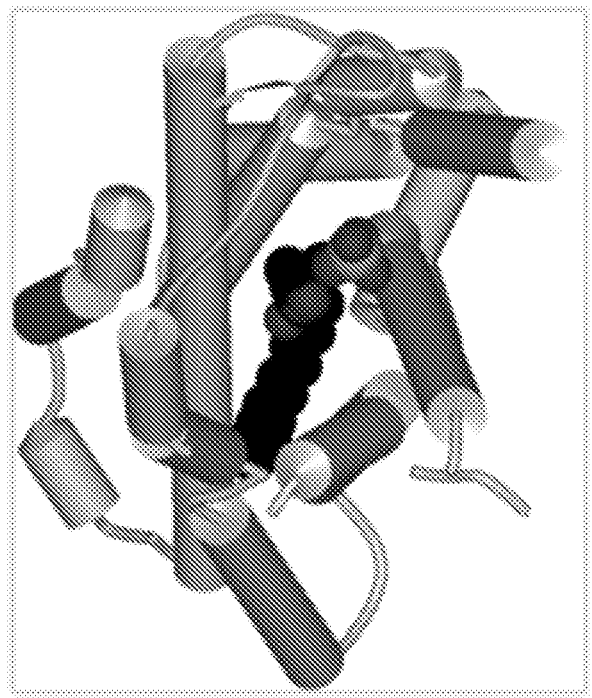
FIG. 14A-B shows the in silico modeling of the binding of compound LPA (18:0) (1-stearoyl-2-hydroxy-sn-glycero-3-phosphate) to the 7TM domain of canine GPR92. (A) Shows a model of the compound binding to GPR92 and (B) shows the putative GPR92 amino acid residues that interact with the binding compound.
Figure 14B:
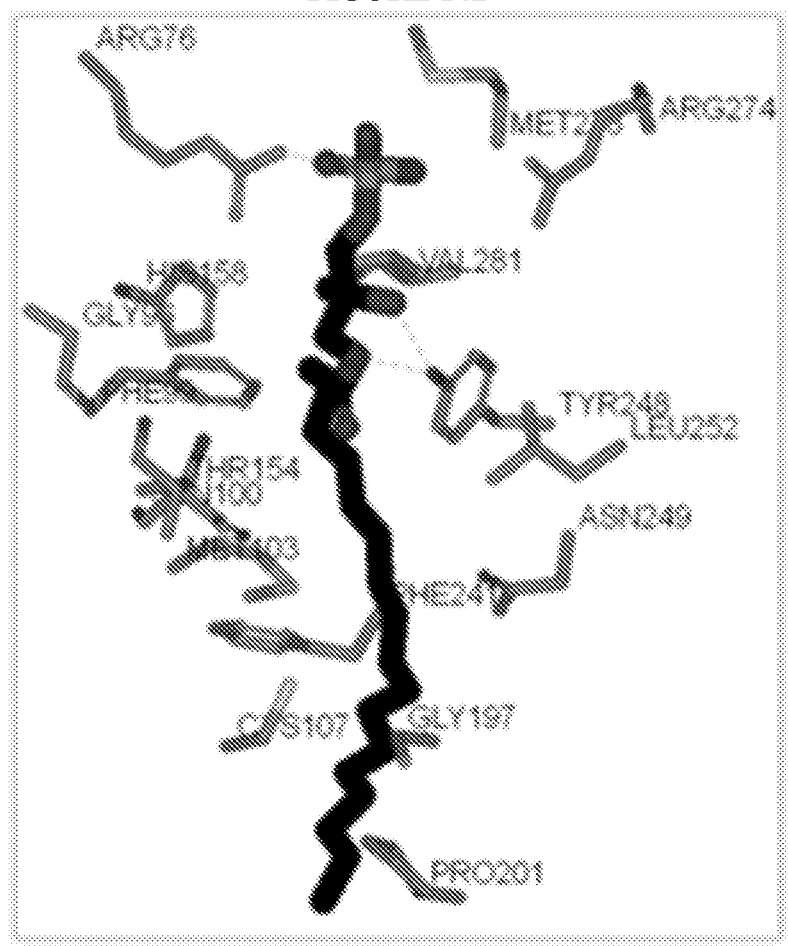

LPA (18:0) (1-stearoyl-2-hydroxy-sn-glycero-3-phosphate), a known potent GPR92 agonist (see Choi et al., Am. J. Physiol. Gastrointest. Liver Physiol., 292: G98-G112 (2007), which is incorporated by reference herein in its entirety), was observed to make potential salt bridge interactions and hydrogen bonds to Arg83 and to Arg281, as well as a hydrogen bond to Tyr255 in feline GPR92 (FIG. 13). Similarly, LPA (18:0) was observed to make potential salt bridge interactions and hydrogen bonds to Arg76 and to Arg274, as well as a hydrogen bond to Tyr248 in canine GPR92 (FIG. 14). Additionally, the tail of LPA (18:0) penetrated deep into the hydrophobic bottom of the active site, forming an extensive network of hydrophobic contacts with both feline and canine GPR92.

Figure 15A:
FIG. 15A-C shows the in silico modeling of the binding of compound NAG (N-Arachidonylglycine) to the 7TM domain of feline GPR92. (A) Shows the structure of the binding compound, (B) shows a model of the compound binding to GPR92, and (C) shows the putative GPR92 amino acid residues that interact with the binding compound.
Figure 15B:
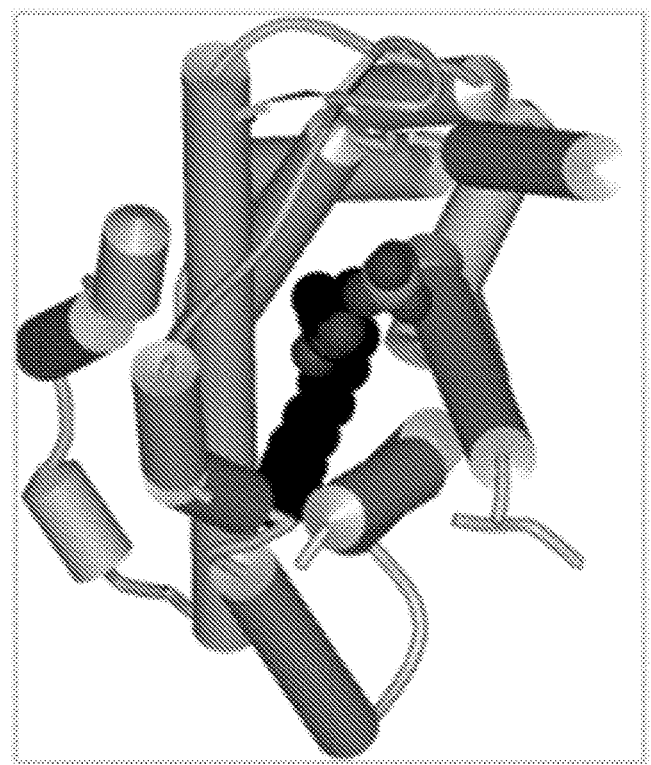
Figure 15C:
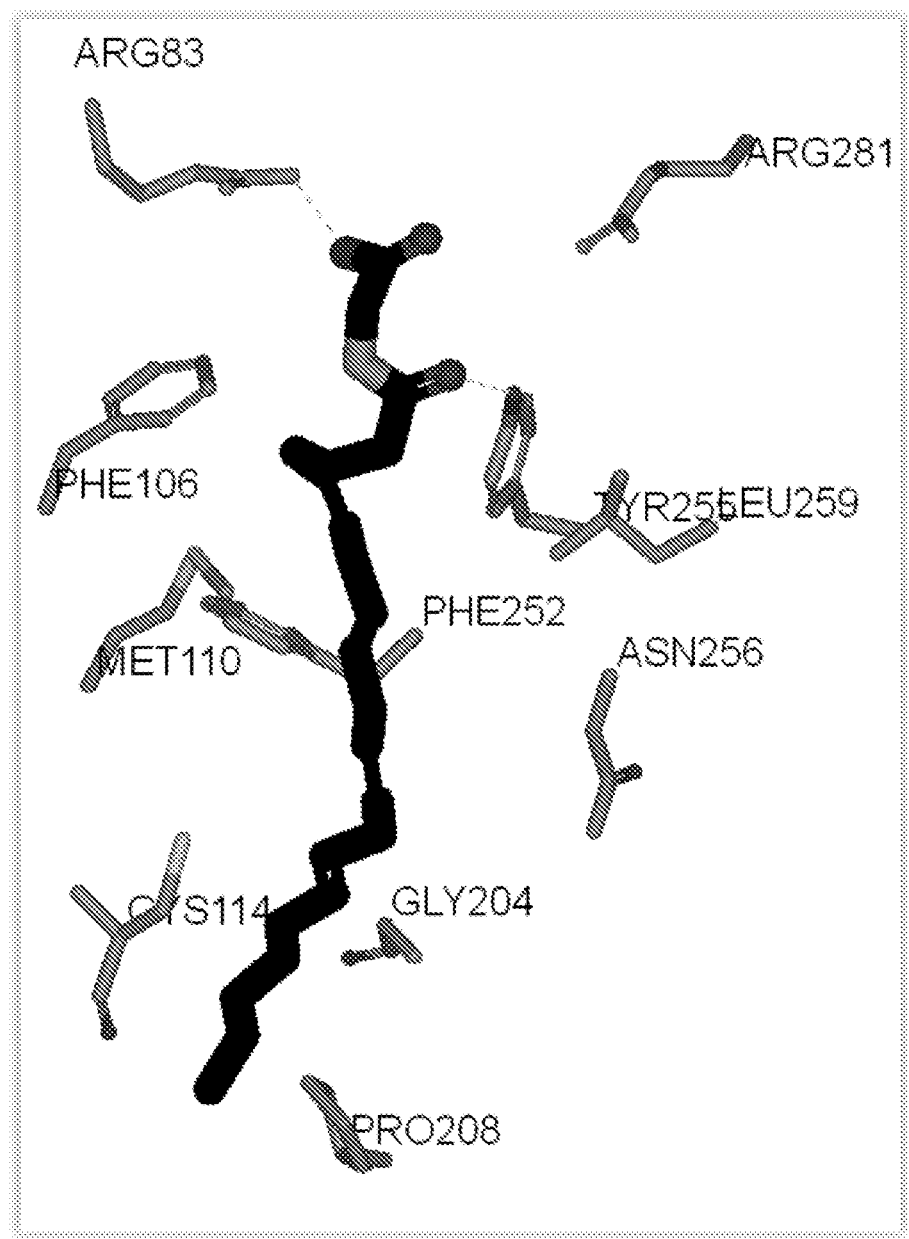
Figure 16A:
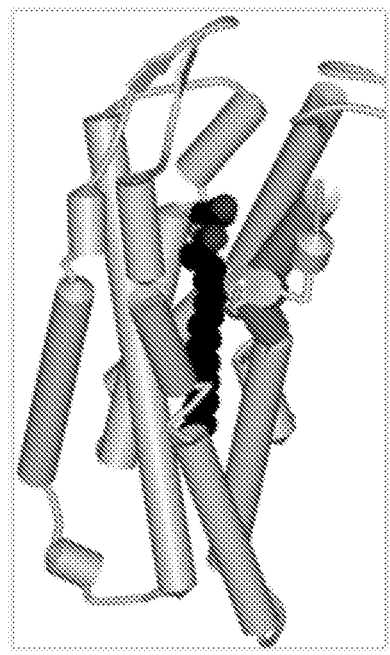
FIG. 16A-B shows the in silico modeling of the binding of compound NAG (N-Arachidonylglycine) to the 7TM domain of canine GPR92. (A) Shows a model of the compound binding to GPR92, and (B) shows the putative GPR92 amino acid residues that interact with the binding compound.
Figure 16B:
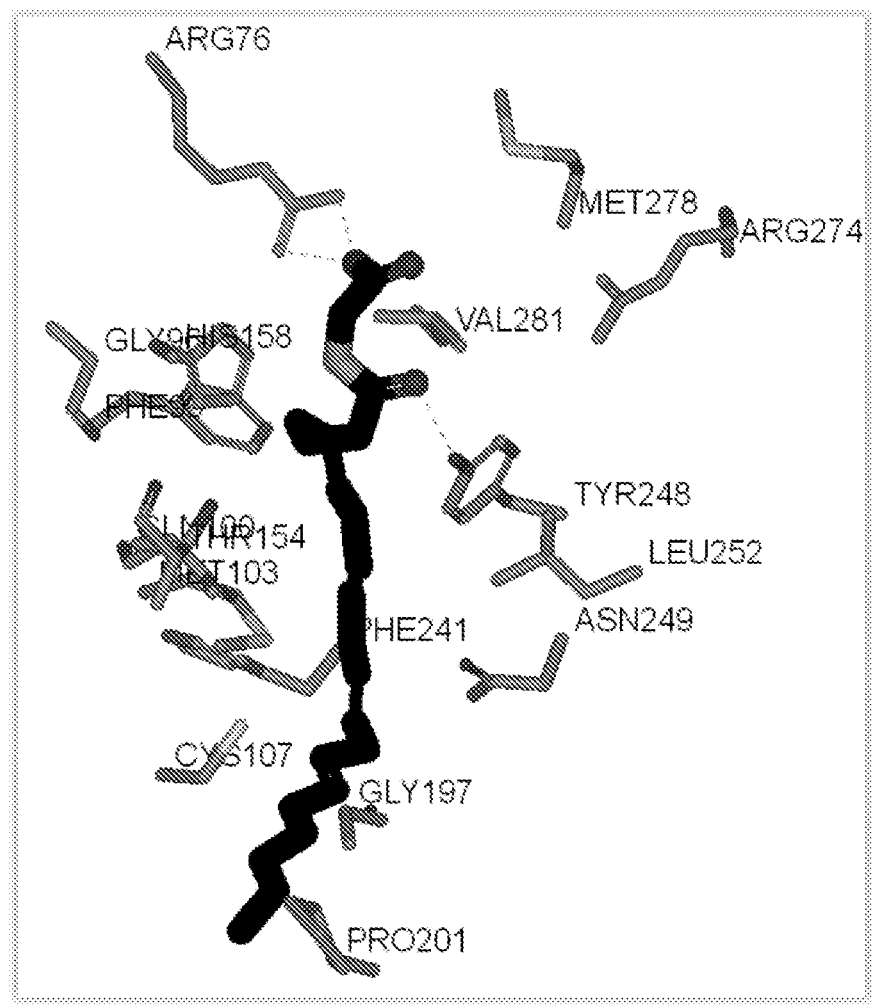

NAG (N-Arachidonylglycine) was observed to make potential salt bridge interactions to Arg83 and to Arg281, as well as a hydrogen bond to Tyr255 in feline GPR92 (FIG. 15). Similarly, NAG was observed to make potential salt bridge interactions to Arg76 and to Arg274, as well as a hydrogen bond to Tyr248 in canine GPR92 (FIG. 16). Additionally, the tail of NAG penetrated deep into the hydrophobic bottom of the active site, forming an extensive network of hydrophobic contacts with both feline and canine GPR92.

Figure 17A:
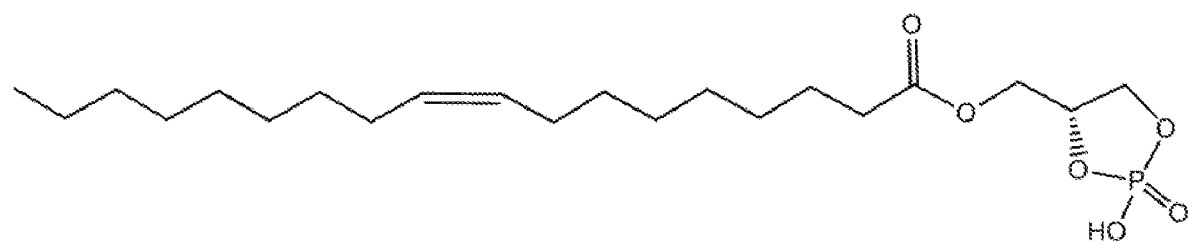
FIG. 17A-C shows the in silico modeling of the binding of compound CPA (18:1) (1-oleoyl-sn-glycero-2,3-cyclic-phosphate) to the 7TM domain of feline GPR92. (A) Shows the structure of the binding compound, (B) shows a model of the compound binding to GPR92, and (C) shows the putative GPR92 amino acid residues that interact with the binding compound.
Figure 17B:
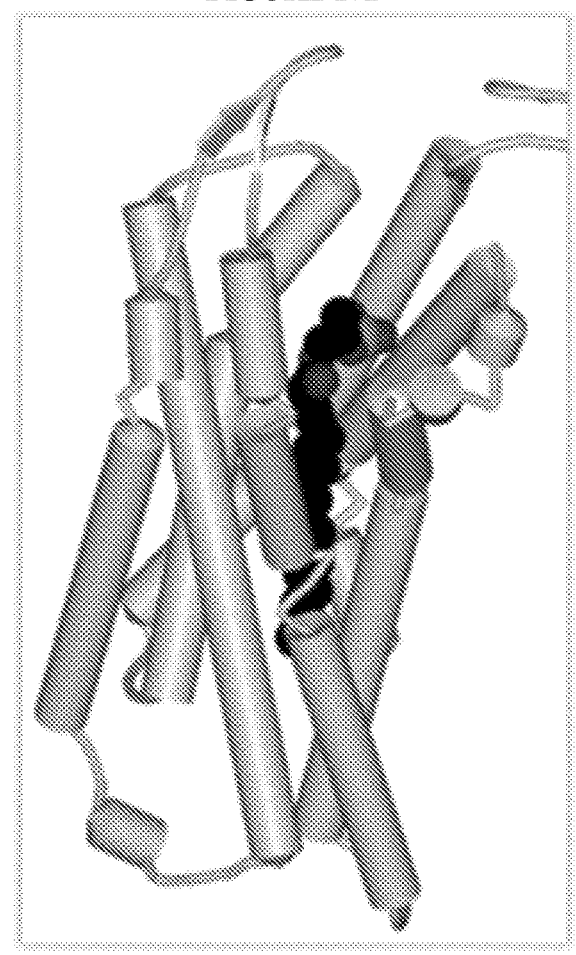
Figure 17C:
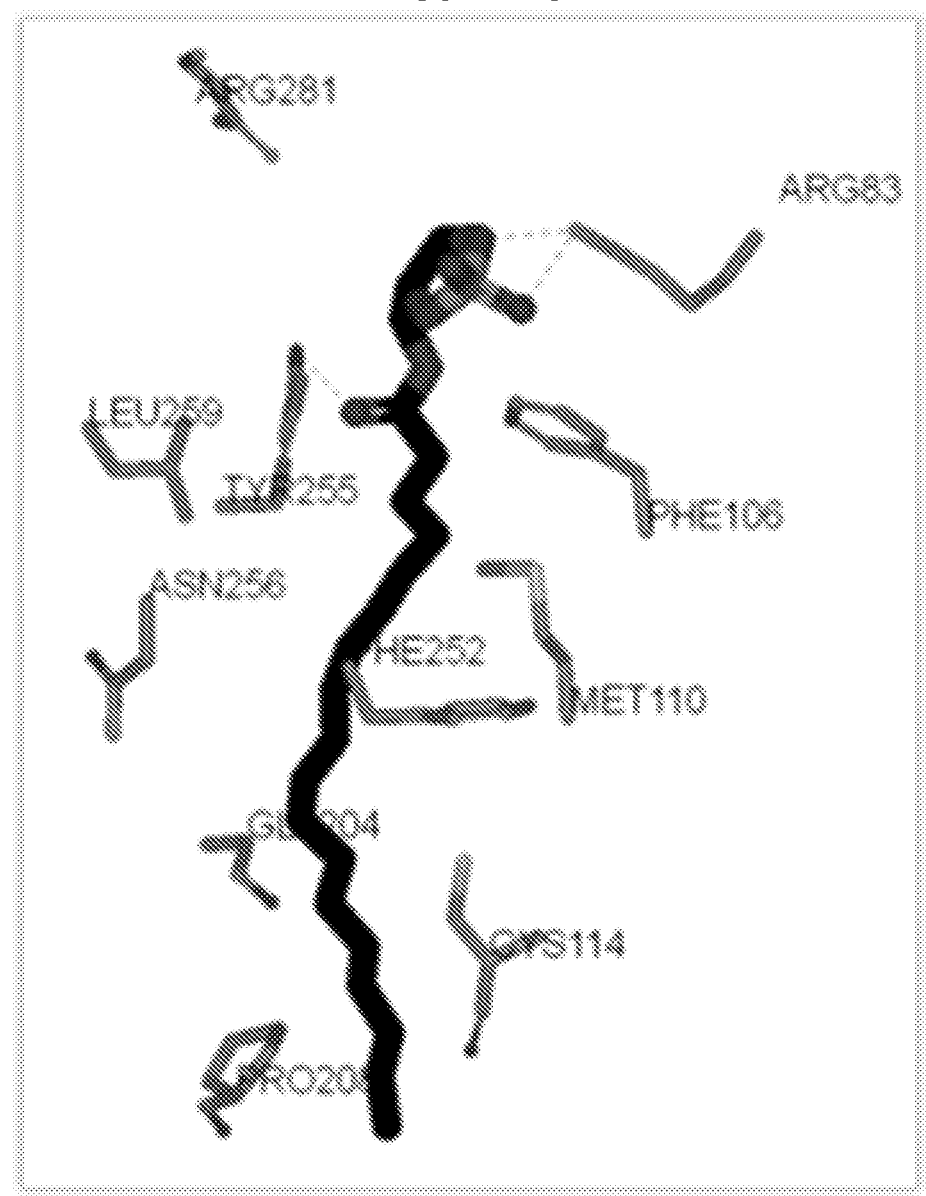
Figure 18A:
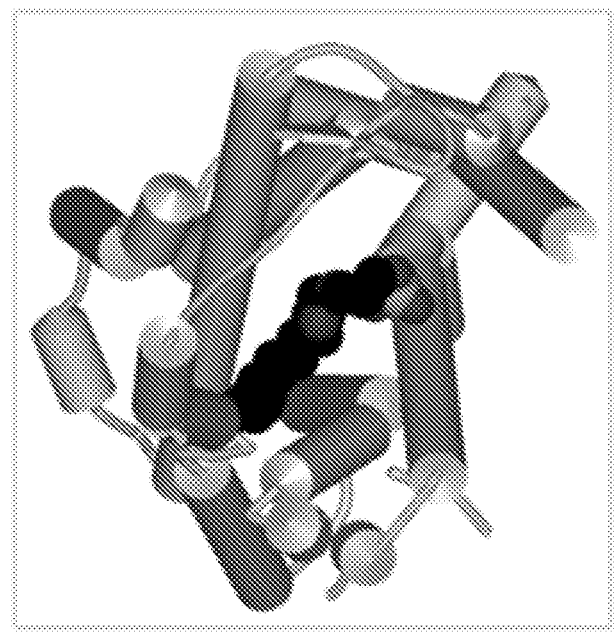
FIG. 18A-B shows the in silico modeling of the binding of compound CPA (18:1) (1-oleoyl-sn-glycero-2,3-cyclic-phosphate) to the 7TM domain of canine GPR92. (A) Shows a model of the compound binding to GPR92 and (B) shows the putative GPR92 amino acid residues that interact with the binding compound.
Figure 18B:
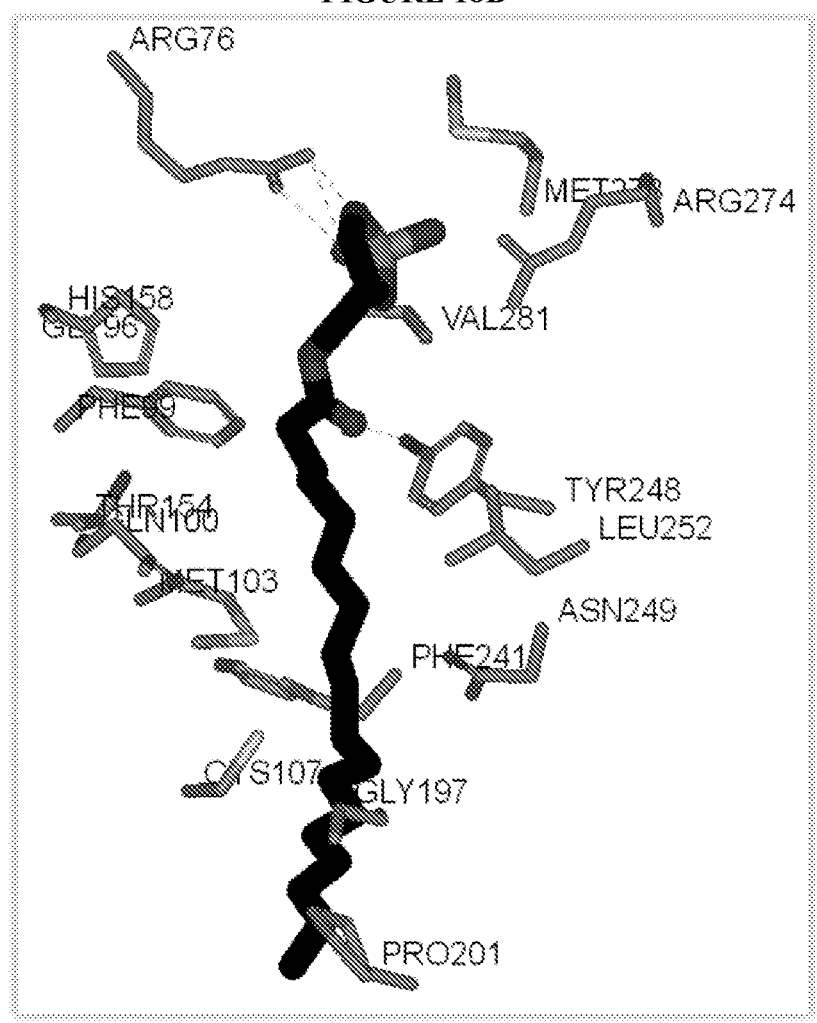

CPA (18:1) (1-oleoyl-sn-glycero-2,3-cyclic-phosphate) was observed to make potential salt bridge interactions and hydrogen bonds to Arg83 and to Arg281, as well as a hydrogen bond to Tyr255 in feline GPR92 (FIG. 17). Similarly, CPA (18:1) was observed to make potential salt bridge interactions to Arg76 and to Arg274, as well as a hydrogen bond to Tyr248 in canine GPR92 (FIG. 18). Additionally, the tail of CPA (18:1) penetrated deep into the hydrophobic cavity of the active site, forming an extensive network of hydrophobic contacts with both feline and canine GPR92.

Example 2—Identification of GPR92 Modulators Using In Vitro Assays

The present example describes an in vitro assay for identifying compounds that modulate feline GPR92 activity.

Summary.

The full length of the feline lysophosphatidic acid receptor 5 (fLPAR5, GPR92) was synthesized and subcloned into a pcDNA3 expression vector. The construct, in parallel with an empty vector, was transfected into the CHO/natClytin reporter cell line. The transfected cells were then antibiotic selected and 2 rounds of limiting dilutions were performed. Positive clones were analysed using the luminescence read-out and lysophosphatidic acid (LPA) reference activators, 14:0 LPA, 16:0 LPA and 18:1 LPA. The best performing CHO/natClytin/fGPR92 clone, K1.4, was completely optimized for ligand pharmacology and assay robustness. Results obtained revealed a functional cell-based assay for fGPR92 suitable for HTS purposes.

Results.

The CHO/natClytin/fGPR92 cell line was generated upon stable transfection of CHO/natClytin cells with an expression construct coding for the feline GPR92 receptor and characterized at FLIPR$^{TETRA}$ instrument using lysophosphatidic acid (LPA) ligands.

Figure 19A:
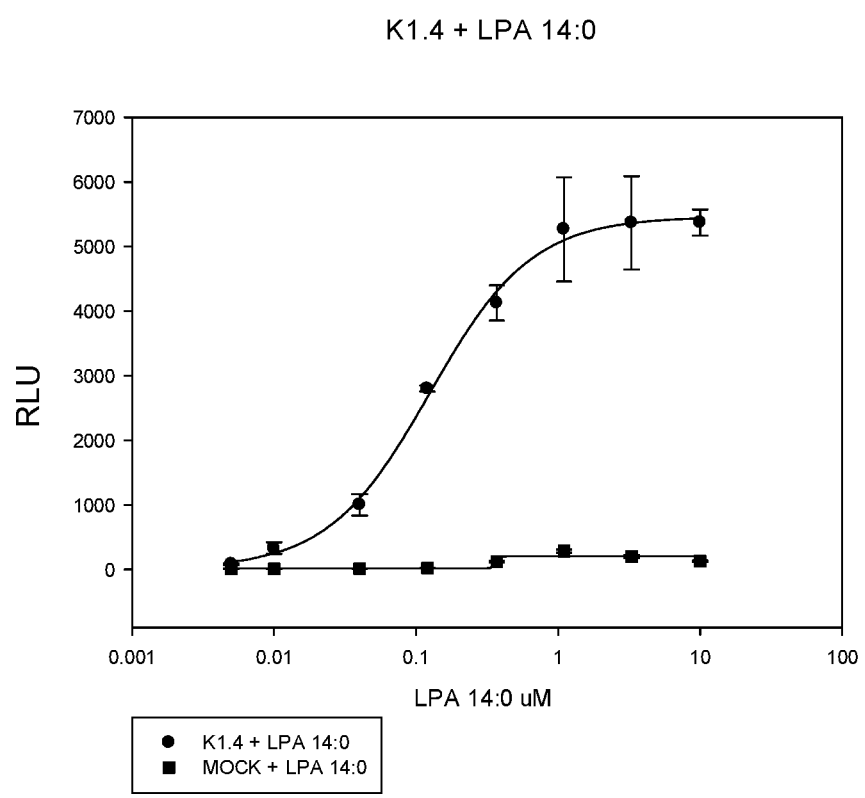
FIG. 19A-C shows the responses of the selected clone K1.4 when tested with LPA 14:0 (1-myristoyl-2-hydroxy-sn-glycero-3-phosphate) (A), LPA 16:0 (1-palmitoyl-2-hydroxy-sn-glycero-3-phosphate) (B), LPA 18:1 (1-oleoyl-2-hydroxy-sn-glycero-3-phosphate) (C). Responses from the mock transfected cell line are also shown.
Figure 19B:
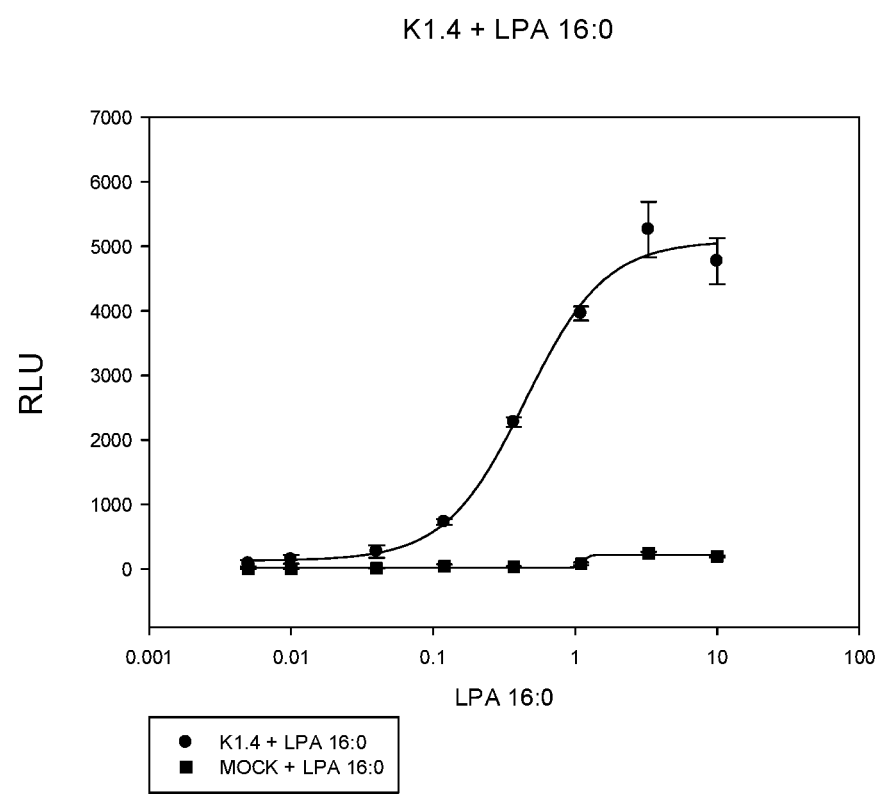
Figure 19C:
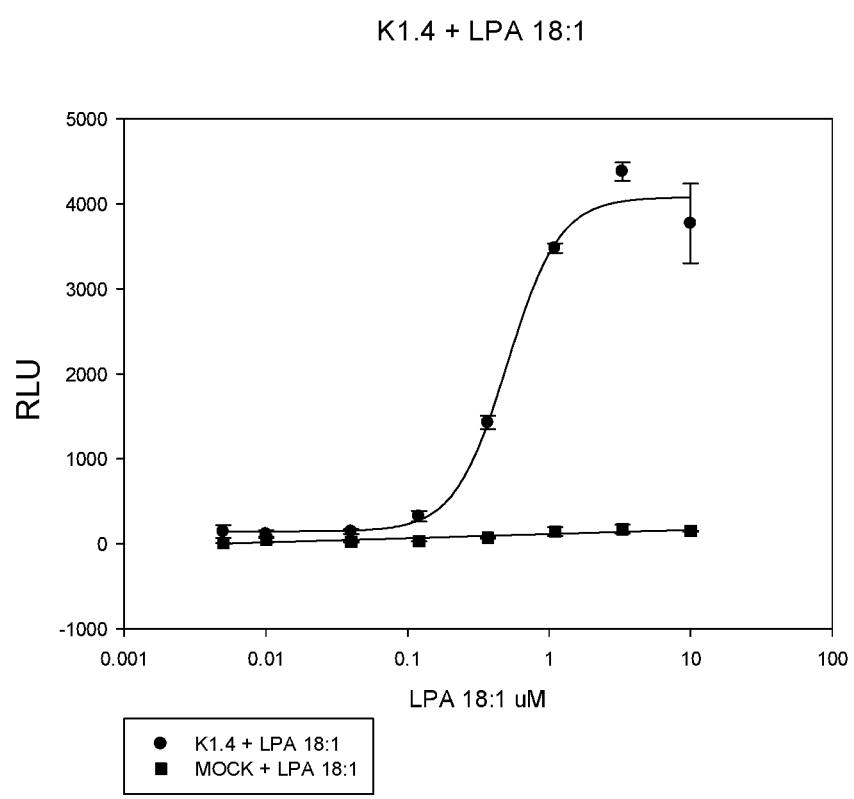

The two best 2° L.D clonesecond limiting dilution clones, K1.2 and 1.4, were optimized for agonist EC50 confirmation, DMSO effect, signal stability over time, freezing/thawing. K1.4 was chosen as final assay clone and then characterized for assay robustness and reproducibility in a multi-plate test (FIG. 19).

Methods:

fGPR92 DNA sequence was synthesized by GeneArt (construct 16AA4JVP_fGPR92_pMK-RQ) with Kozak sequence and 5'BamHI, 3'XhoI extremities. The fGPR92 was extracted with BamHI/XhoI and unidirectionally cloned in pcDNA3.1 expression vector opened with the same restriction enzymes. Analysis for screening of positive clones was performed with PvuI and from the clones with the correct DNA fragmentation (4179+2324 pb), clone K3 was selected and confirmed by sequencing of the whole insert region.

The full-length coding sequence of the feline LPAR5 was cloned into pcDNA3.1 expression vector. The pcDNA3.1_fLPAR5 construct was stably transfected into CHO/natClytin cell line, in parallel with the pcDNA3.1 empty vector. Transfected cells were grown in the presence of 2 mg/mL G418. After antibiotic selection and clone pool test, a 1° first limiting dilution of the transfected target and mock pools was performed and then analyzed by incubating the cells with coelenterazine. Positive clone selection was performed by stimulating the cells with 14:0 and 16:0 LPA agonists. The receptor-dependent luminescence was measured using the FLIPR$^{TETRA}$ instrument.

10 selected 1° first limiting dilution clones, in parallel with 4 mock clones, were analyzed for their response to different agonists: 14:0 LPA, 16:0 LPA and 18:1 LPA. 1° First limiting dilution selected clones showed good and specific dose-responses with all tested ligands tested.

3 best responding clones underwent a 2° second limiting dilution. Clone selection was performed using luminescent read-out upon stimulation with 14:0 LPA and 16:0 LPA agonists. Then the 6 best 2° second limiting dilution clones were further characterized with different agonists: 14:0 LPA, 16:0 LPA and 18:1 LPA.

The two best 2° second L.D clones, K1.2 and 1.4, were optimized for agonist EC50 confirmation, DMSO effect, signal stability over time, and freezing/thawing. K1.4 was chosen as final assay clone and then characterized for assay robustness and reproducibility in a multi-plate test.

HTS assay robustness and reproducibility was evaluated using 14:0 LPA and 16:0 LPA on the K1.4 final clone. 10,000 cells/well, 6×384 MTPs, were seeded and 24 hours later cells were incubated in Tyrode's buffer with 10 µM coelenterazine (20 µL/w) for 3 hours at 37° C. and for 1 hour at RT. Luminescence measurement for 1 minute was performed at 280000 gain of sensitivity after single injection (2× final concentration, 20 µL/well) as follows:

14:0 LPA dose-response (3 µM, 1 µM, 0.3 µM, 0.1 µM, 30 nM, 10 nM, 3 nM, 1 nM) in Tyrode's plus 0.5% DMSO.

Tyrode's buffer plus 0.5% DMSO (Control Ref) and 14:0 LPA $EC_{100}$ value (3 µM, Signal Ref) in Tyrode's buffer plus 0.5% DMSO.

16:0 LPA dose-response (10 µM, 3 µM, 1 µM, 0.3 µM, 0.1 µM, 30 nM, 10 nM, 3 nM) in Tyrode's buffer plus 0.5% DMSO.

Tyrode's buffer plus 0.5% DMSO (Control Ref) and 16:0 LPA $EC_{100}$ value (10 µM, Signal Ref) in Tyrode's buffer plus 0.5% DMSO.

$FLIPR^{TETRA}$ measurements were analysed with Screenworks© software (Molecular Devices, Version 3.0.1.4) and data were exported as Maximum statistics of Absolute Response (RLU) calculated after compound injection. RLU is obtained applying "Subtract Bias on Sample n" (where n=Time point of compound injection).

Mean and standard deviation values were calculated on the exported data with Microsoft Excel software, then values were used to create sigmoidal dose-response curves (variable slope) or histograms with GraphPad PRISM® software (Version 7).

The obtained values were used to calculate $EC_{50}$ values according to the following formula:

$$EC_X = [(X/100-X)1/\text{HillSlope}]*EC_{50}$$

The robust Z prime (rZ'), the Intraplate Variability and the Interplate Variability are calculated onto minimum (Control Reference, CR) well signals and maximum (Signal Reference, SR) well signals, according to the following formula:

$$RZ' = 1 - \frac{3*(RSD_{CR} + RSD_{SR})}{|\langle CR \rangle - \langle SR \rangle|}$$

$$\text{VariabilityIntraplate\_CR}p) = \frac{RSD_{CR}(p)}{|\langle SR \rangle - \langle CR \rangle|} * 100$$

$$\text{VariabilityIntraplate\_SR}p) = \frac{RSD_{SR}(p)}{|\langle SR \rangle - \langle CR \rangle|} * 100$$

$$\text{VariabilityInterplate\_CR}p,d) = \frac{\langle CR(p) \rangle - \overline{\langle CR(p,d) \rangle}}{|\overline{\langle CR(p,d) \rangle} - \overline{\langle SR(p,d) \rangle}|} * 100$$

$$\text{VariabilityInterplate\_SR}p,d) = \frac{\langle SR(p) \rangle - \overline{\langle SR(p,d) \rangle}}{|\overline{\langle CR(p,d) \rangle} - \overline{\langle SR(p,d) \rangle}|} * 100$$

Cell Lines, Media and Culture Conditions.

CHO/natClytin cells were cultured in medium DMEM F-12 (1:1) MIXTURE (BioWittaker cat. BE04-687F/U1) supplemented with 5 mL of 100 mM Sodium Pyruvate (BioWittaker cat. BE13-115E), 25 mL of 7.5% Sodium Bicarbonate (BioWittaker cat. BE17-613E), 6.5 mL of 1 M Hepes (BioWittaker cat. BE17-737E), 5 mL of 100× Penicillin/Streptomycin (BioWittaker cat. DE17-602E), 50 mL of Fetal Bovine Serum (Euroclone cat. No: ECS 0180L) and 0.25 mL of 10 mg/mL Puromycin (InvivoGen cat. Ant-pr-1) as natClytin photoprotein resistance.

CHO/natClytin/fLPAR5 cells were selected using standard medium supplemented with 2 mg/mL G418 (InvivoGen cat. Ant-gn-5) and then maintained in standard medium supplemented with 1 mg/mL G418.

Cell Maintenance and Propagation.

Standard propagation conditions consist of plating $3 \times 10^5$ cells in T75 flask, recovering about $8\text{-}10 \times 10^6$ cells/T75 flask (after 3-4 days). As an alternative, a 70-80% confluent cell population can be diluted 1:20-1:30 every 3-4 days. Standard seeding conditions for the experiments in 384 MTPs were 10,000 cells/well seeded and analysed 24 hours later. Cells were split by gentle washing with PBS, followed by 5 min incubation at 37° C. with trypsin-EDTA solution. Detached cells were diluted with complete medium, counted using the BECKMAN COULTER Z1TM Particle Counter and the desired number of cells is plated into a new flask or used for adherent experiments.

Freezing medium was prepared as follows: 90% FBS+ 10% DMSO. Freezing conditions were: $8\text{-}10 \times 10^6$ cells (70-80% confluence) in 1 mL of freezing medium. Thawing procedure was: thaw cells rapidly by removing from liquid nitrogen and immediately immersing in a 37° C. water bath. Immediately after ice has thawed, sterilize the exterior of the vial with 70% ethanol, or equivalent: transfer contents of the vial to a T75 flask containing complete medium. Place the flask in a humidified incubator at 37° C. with 5% $CO_2$. Check the recovery the day after and subculture when adherent cells reach 80% of confluence.

Buffers and Ligands.

Tyrode's buffer: in house solution (130 mM NaCl, 5 mM KCl, 2 mM $CaCl_2$, 1 mM $MgCl_2$, 5 mM $NaHCO_3$, 20 mM Hepes in water at pH 7.4; sterile filtered and autoclaved).

LPA ligands: 14:0 LPA (1-myristoyl-2-hydroxy-sn-glycero-3-phosphate, sodium salt), Avanti Polar Lipids, cat. 857120P; 16:0 LPA (1-palmitoyl-2-hydroxy-sn-glycero-3-phosphate, sodium salt), Avanti Polar Lipids, cat. 857123P; 18:1 LPA (1-oleoyl-2-hydroxy-sn-glycero-3-phosphate, sodium salt), Avanti Polar Lipids, cat. 857130P.

5 mM stock solution prepared in 100% DMSO after warming at 37° C. and sonicating for 20 minutes in the waterbath Branson 3200 sonicator. Aliquots stored in glass-bottles at −20° C. Dose-responses were always prepared in Tyrode buffer supplemented with 0.01% BSA fatty acid free and immediately used. Bovine Serum Albumin (BSA) fatty acid free: Sigma, cat. A8806, 1% freshly prepared in Tyrode buffer. Coelenterazine: PharmaTech Int., cat. CAS 55779-48-1, 10 mM stock solution prepared in DMSO-Glutathione, stored in aliquots at −20° C. Working solutions were freshly prepared in Tyrode's buffer.

Instrumentation and Disposables.

The experimental activities were performed using the ICCD camera $FLIPR^{TETRA}$ (Molecular Devices). The analysis was performed in 384-well polystyrene assay plates. Cell culture flask: 75 $cm^2$ flask CORNING, cat. 430641. Test plates: 384-well tissue culture treated microplates (MTP), black/clear bottom plates: MATRIX cat. 4332. Compound plates: 384-well polypropylene assay plates, V bottom: MATRIX, cat. 4312.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

We claim:

1. A method for identifying a composition that modulates the activity of a GPR92 receptor comprising:
   (a) contacting a test agent with a GPR92 receptor,
   (b) determining the activity of the GPR92 receptor, and
   (c) selecting as the composition, a test agent that increases the activity of the GPR92 receptor,
   wherein the GPR92 receptor is selected from the group consisting of a feline GPR92 receptor comprising the amino acid sequence set forth in SEQ ID NO: 4 and a canine GPR92 receptor comprising the amino acid sequence set forth in SEQ ID NO: 5.

2. A method for identifying a composition that modulates the activity of a GPR92 receptor comprising:
   (a) contacting a test agent with a GPR92 receptor,
   (b) detecting an interaction between the test agent and one or more amino acids in a 7 transmembrane domain (7TM) of the GPR92 receptor, and
   (c) selecting as the composition, a test agent that interacts with one or more of the amino acids,
   wherein the GPR92 receptor is selected from the group consisting of a feline GPR92 receptor comprising the amino acid sequence set forth in SEQ ID NO: 4 and a canine GPR92 receptor comprising the amino acid sequence set forth in SEQ ID NO: 5.

3. The method of claim 2, wherein the GPR92 receptor is the feline GPR92 receptor comprising the amino acid sequence set forth in SEQ ID NO: 4, and wherein the one or more amino acids in the 7TM is selected from the group consisting of Arg83 on Helix 2; Gly103, Phe106, Gln107, Met110, and/or Cys114 on Helix 3; Thr161 and/or His165 on Helix 4; Ala200, Gly204, and/or Pro208 on Helix 5; Phe248, Phe252, Tyr255, Asn256, and/or Leu259 on Helix 6; Arg281, Met285, and/or Val288 on Helix 7; and/or Glu182 on the second extracellular (EC2) loop.

4. The method of claim 2, wherein the GPR92 receptor is the canine GPR92 receptor comprising the amino acid sequence set forth in SEQ ID NO: 5, and wherein the one or more amino acids in the 7TM is selected from the group consisting of Arg76 on Helix 2; Gly96, Phe99, Gln100, Met103, and/or Cys107 on Helix 3; Thr154 and/or His158 on Helix 4; Ala193, Gly197, and/or Pro201 on Helix 5; Phe241, Phe245, Tyr248, Asn249, and/or Leu252 on Helix 6; Arg274, Met278, and/or Val281 on Helix 7; and/or Glu175 on the EC2 loop.

5. The method of claim 2, further comprising determining the activity of the GPR92 receptor after step (a).

6. The method of claim 2, further comprising contacting a GPR92 receptor ligand to the GPR92 receptor.

7. The method of claim 2, wherein step (c) further comprises selecting as the composition, a test agent that increases the activity of the GPR92 receptor.

8. The method of claim 2, wherein the interaction is determined by site directed mutagenesis, x-ray crystallography, x-ray spectroscopy, Nuclear Magnetic Resonance (NMR), cross-linking assessment, mass spectroscopy, electrophoresis, displacement assay, and combinations thereof.

9. The method of claim 1, wherein the GPR92 receptor is expressed by a cell, and wherein the test agent is contacted to the cell.

10. The method of claim 9, wherein the cell expresses a calcium-binding photoprotein.

11. The method of claim 10, wherein the calcium-binding photoprotein is selected from the group consisting of clytin, aequorin, obelin, any recombinant or isolated versions thereof, and any combinations thereof.

12. The method of claim 1, wherein the determining the activity of the GPR92 receptor comprises monitoring an intracellular calcium level by a luminescence detection or a fluorescence detection.

13. The method of claim 12, wherein the fluorescence detection comprises a calcium sensitive fluorescent dye selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

14. The method of claim 5, wherein the GPR92 receptor is expressed by a cell, and wherein the test agent is contacted to the cell.

15. The method of claim 14, wherein the cell expresses a calcium-binding photoprotein.

16. The method of claim 15, wherein the calcium-binding photoprotein is selected from the group consisting of clytin, aequorin, obelin, any recombinant or isolated versions thereof, and any combinations thereof.

17. The method of claim 5, wherein the determining the activity of the GPR92 receptor comprises monitoring an intracellular calcium level by a luminescence detection or a fluorescence detection.

18. The method of claim 17, wherein the fluorescence detection comprises a calcium sensitive fluorescent dye selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

* * * * *

SEQUENCE LISTING

<160> NUMBER OF SEQ ID NOS: 6

<210> SEQ ID NO 1
<211> LENGTH: 1122
<212> TYPE: DNA
<213> ORGANISM: Felis catus

<400> SEQUENCE: 1

| | | | | | |
|---|---|---|---|---|---|
| atgttgccca | actctaccaa | cagttctgtt | cccnctgcca | acggttctgt | tccccgtgc | 60 |

```
atgttgccca actctaccaa cagttctgtt cccnctgcca acggttctgt tccccgtgc       60 cccgactacc ggcccaccca ccgcctgcac atggtggcct acagcctggt gctggccgca     120
gggctccccc tcaacgcgct ggccctctgg gtcttcctgc gcgcgctgcg agtgcactcc     180
gtcgtgagcg tgtacatgtg caacctggcg gccagcgacc tgctcttcac cctctcgctg     240
cccgtgcgca tctcctacta cgccctgcac tactggccct ctccgacct cctgtgccag      300 acggcgggcg ccatcttcca gacgaacatg tacggcagct gcatcttcct gactctcatc    360
aacgtggacc gctacgcggc catcgtgcac ccgctgcggc tgcgccacct gcggcggccc    420
cgcgtggcgc ggctgctctg cctgggagtg tgggcgctca tcctcgtgtt cgctgtgccc    480
accgtcctgg tgcacaggcc ctcgtcctgc agctacggcg gcggccaggt gcgcctgtgc    540
ttcgagagct tcggcgacag gctgtggaag ggcgggctgc tgccgctcgt gctgctggcc    600
gaggcgctgg gcttcctgct gcccctggtg gcggtgctct actcgtcggg ccgggtcttc    660
tggaccctgg cgcggcccga cgccacgcag agccagcggc ggcggaagac cgtgcgcctc    720
ctgctggcca acctcgtcat cttcctgctg tgcttcgtgc cctacaacgc cacgctggcg    780
gtgtacgggc tgctgcgggg caacctggtg gcggcgaaca gcaaggtctg cgatcgggtg    840
cgcggggtgc tgatggtgat ggtgctgttg ccggcgcca actgcgtgct agaccctctg    900
gtgtattact tcagcgccga gggtttccgc aacaccctgc gaggcctggg cactccgaac    960
cgcgccagga ccttggccac caacggggct caggggcgc tcgccgaaca gcccactgag  1020
accacttaca tcaccacccc ggctaccgcc gaacaggggc tgctcaggcc ctccaacgtg  1080
gggacaccct aacccagct ccccgaggac tcggcctct ga                        1122
```

<210> SEQ ID NO 2
<211> LENGTH: 1101
<212> TYPE: DNA
<213> ORGANISM: Canis familiaris

<400> SEQUENCE: 2

```
atgctgaccg cctcggccaa cagctccgtc cccccatgcc ccgactaccg ggtcacccac       60
cgcctgcaca tggtggccta cagcctggtc ctggccgcgg ggctccccct caacgcgctg      120
gccctctggg tcttcctgcg cgcgctgcgc gtgcactccg tggtcagcgt gtacatgtgc      180
aacctggcgg ccagcgacct gctcttcacg ctctcgctgc ccgtgcgcat tcctactac      240 gccctgcacc actggcccct ctccgacctc ctgtgtcaga cggccggcgc cgtcttccag      300
accaacatgt acggcagctg catcttcctg accctcatta acgtggaccg ctacgcggcc      360
atcgtgcacc cactgcggct gcgccacctg cggcggcccc gcgtggcgcg gctgctgtgc     420
ctgggcgtgt gggcgctcat cctggtgttc gccgtgccca ccgtcctggt gcaccggccc     480
tcgccctgca gctacgacgg cggccggcg cggctgtgct cgagagcttc ggcgacaag       540 ctgtggaagg gcgggctgct gccgctcgtg ctgctggccg aggcgctggg cttcctgctg     600
ccgctcgcgg ccatgctcta ctcgtcgggc cgggtcttct ggaccctggc gcggcccgac    660
gccacgcgga gccggcggcg gcggaagacc gtgcgcctcc tgctggccaa cctcgtcatc    720
```

```
ttcctgctgt gcttcgtgcc ctacaacgcc acgctggccg tctacgggct gctgcggggc     780
aacctggtgg cggccggcag cgaggccagc gaccgcgtgc gccaggtgct catggtgatg     840
gtgctgctgg ccagcgccaa ctgcgtgctg acccgctgg tgtactactt cagcgccgag      900
ggcttccgca caccctgcg cggcctgggc acttggcacc gtgccaggac cttggccacc      960
aacggggcgc aggggggcgct ggccgagcgg ctcaccgaga ccacctgcat cgccgggccg   1020
gctcccgcca gccgagagcc tcccgcgtcc tccccggggg ggacgccctt gacccagcgc   1080
cgggaggact cggccctctg a                                               1101
```

<210> SEQ ID NO 3
<211> LENGTH: 1119
<212> TYPE: DNA
<213> ORGANISM: Homo sapiens

<400> SEQUENCE: 3

```
atgttagcca acagtcctc aaccaacagt tctgttctcc cgtgtcctga ctaccgacct       60
acccaccgcc tgcacttggt ggtctacagc ttggtgctgg ctgccgggct ccccctcaac     120
gcgctagccc tctgggtctt cctgcgcgcg ctgcgcgtgc actcggtggt gagcgtgtac     180
atgtgtaacc tggcggccag cgacctgctc ttcaccctct cgctgcccgt tcgtctctcc     240
tactacgcac tgcaccactg gcccttcccc gacctcctgt gccagacgac gggcgccatc     300
ttccagatga acatgtacgg cagctgcatc ttcctgatgc tcatcaacgt ggaccgctac     360
gccgccatcg tgcacccgct gcgactgcgc cacctgcggc ggccccgcgt ggcgcggctg     420
ctctgcctgg gcgtgtgggc gctcatcctg gtgtttgccg tgcccgccgc ccgcgtgcac     480
aggccctcgc gttgccgcta ccgggacctc gaggtgcgcc tatgcttcga gagcttcagc     540
gacgagctgt ggaaaggcag gctgctgccc ctcgtgctgc tggccgaggc gctgggcttc     600
ctgctgcccc tggcggcggt ggtctactcg tcgggccgag tcttctggac gctggcgcgc     660
cccgacgcca cgcagagcca gcggcggcgg aagaccgtgc gcctcctgct ggctaacctc     720
gtcatcttcc tgctgtgctt cgtgcccta aacagcacgc tggcggtcta cgggctgctg     780
cggagcaagc tggtggcggc cagcgtgcct gcccgcgatc gcgtgcgcgg ggtgctgatg     840
gtgatggtgc tgctggccgg cgccaactgc gtgctggacc cgctggtgta ctactttagc     900
gccgagggct tccgcaacac cctgcgcggc ctgggcactc cgcaccgggc caggacctcg     960
gccaccaacg ggacgcgggc ggcgctcgcg caatccgaaa ggtccgccgt caccaccgac    1020
gccaccaggc cggatgccgc cagtcagggg ctgctccgac cctccgactc ccactctctg    1080
tcttccttca cacagtgtcc ccaggattcc gccctctga                            1119
```

<210> SEQ ID NO 4
<211> LENGTH: 373
<212> TYPE: PRT
<213> ORGANISM: Felis catus

<400> SEQUENCE: 4

```
Met Leu Pro Asn Ser Thr Asn Ser Ser Val Pro Pro Ala Asn Gly Ser
1               5                   10                  15

Val Pro Pro Cys Pro Asp Tyr Arg Pro Thr His Arg Leu His Met Val
                20                  25                  30

Ala Tyr Ser Leu Val Leu Ala Ala Gly Leu Pro Leu Asn Ala Leu Ala
            35                  40                  45

Leu Trp Val Phe Leu Arg Ala Leu Arg Val His Ser Val Val Ser Val
```

```
            50                  55                  60
Tyr Met Cys Asn Leu Ala Ala Ser Asp Leu Leu Phe Thr Leu Ser Leu
 65                  70                  75                  80

Pro Val Arg Ile Ser Tyr Tyr Ala Leu His Tyr Trp Pro Phe Ser Asp
                 85                  90                  95

Leu Leu Cys Gln Thr Ala Gly Ala Ile Phe Gln Thr Asn Met Tyr Gly
            100                 105                 110

Ser Cys Ile Phe Leu Thr Leu Ile Asn Val Asp Arg Tyr Ala Ala Ile
            115                 120                 125

Val His Pro Leu Arg Leu Arg His Leu Arg Arg Pro Arg Val Ala Arg
            130                 135                 140

Leu Leu Cys Leu Gly Val Trp Ala Leu Ile Leu Val Phe Ala Val Pro
145                 150                 155                 160

Thr Val Leu Val His Arg Pro Ser Ser Cys Ser Tyr Gly Gly Gly Gln
                165                 170                 175

Val Arg Leu Cys Phe Glu Ser Phe Gly Asp Arg Leu Trp Lys Gly Gly
            180                 185                 190

Leu Leu Pro Leu Val Leu Leu Ala Glu Ala Leu Gly Phe Leu Leu Pro
            195                 200                 205

Leu Val Ala Val Leu Tyr Ser Ser Gly Arg Val Phe Trp Thr Leu Ala
210                 215                 220

Arg Pro Asp Ala Thr Gln Ser Gln Arg Arg Lys Thr Val Arg Leu
225                 230                 235                 240

Leu Leu Ala Asn Leu Val Ile Phe Leu Leu Cys Phe Val Pro Tyr Asn
                245                 250                 255

Ala Thr Leu Ala Val Tyr Gly Leu Leu Arg Gly Asn Leu Val Ala Ala
            260                 265                 270

Asn Ser Lys Val Cys Asp Arg Val Arg Gly Val Leu Met Val Met Val
            275                 280                 285

Leu Leu Ala Gly Ala Asn Cys Val Leu Asp Pro Leu Val Tyr Tyr Phe
            290                 295                 300

Ser Ala Glu Gly Phe Arg Asn Thr Leu Arg Gly Leu Gly Thr Pro Asn
305                 310                 315                 320

Arg Ala Arg Thr Leu Ala Thr Asn Gly Ala Gln Gly Ala Leu Ala Glu
                325                 330                 335

Gln Pro Thr Glu Thr Thr Tyr Ile Thr Thr Pro Ala Thr Ala Glu Gln
            340                 345                 350

Gly Leu Leu Arg Pro Ser Asn Val Gly Thr Pro Leu Thr Gln Leu Pro
            355                 360                 365

Glu Asp Ser Ala Leu
            370

<210> SEQ ID NO 5
<211> LENGTH: 366
<212> TYPE: PRT
<213> ORGANISM: Canis familiaris

<400> SEQUENCE: 5

Met Leu Thr Ala Ser Ala Asn Ser Ser Val Pro Pro Cys Pro Asp Tyr
  1               5                  10                  15

Arg Val Thr His Arg Leu His Met Val Ala Tyr Ser Leu Val Leu Ala
                 20                  25                  30

Ala Gly Leu Pro Leu Asn Ala Leu Ala Leu Trp Val Phe Leu Arg Ala
             35                  40                  45
```

Leu Arg Val His Ser Val Val Ser Val Tyr Met Cys Asn Leu Ala Ala
 50                  55                  60

Ser Asp Leu Leu Phe Thr Leu Ser Leu Pro Val Arg Ile Ser Tyr Tyr
 65                  70                  75                  80

Ala Leu His His Trp Pro Phe Ser Asp Leu Leu Cys Gln Thr Ala Gly
                 85                  90                  95

Ala Val Phe Gln Thr Asn Met Tyr Gly Ser Cys Ile Phe Leu Thr Leu
                100                 105                 110

Ile Asn Val Asp Arg Tyr Ala Ala Ile Val His Pro Leu Arg Leu Arg
            115                 120                 125

His Leu Arg Arg Pro Arg Val Ala Arg Leu Leu Cys Leu Gly Val Trp
130                 135                 140

Ala Leu Ile Leu Val Phe Ala Val Pro Thr Val Leu Val His Arg Pro
145                 150                 155                 160

Ser Pro Cys Ser Tyr Asp Gly Gly Arg Ala Arg Leu Cys Phe Glu Ser
                165                 170                 175

Phe Gly Asp Lys Leu Trp Lys Gly Gly Leu Leu Pro Leu Val Leu Leu
                180                 185                 190

Ala Glu Ala Leu Gly Phe Leu Leu Pro Leu Ala Ala Met Leu Tyr Ser
                195                 200                 205

Ser Gly Arg Val Phe Trp Thr Leu Ala Arg Pro Asp Ala Thr Arg Ser
    210                 215                 220

Arg Arg Arg Arg Lys Thr Val Arg Leu Leu Leu Ala Asn Leu Val Ile
225                 230                 235                 240

Phe Leu Leu Cys Phe Val Pro Tyr Asn Ala Thr Leu Ala Val Tyr Gly
                245                 250                 255

Leu Leu Arg Gly Asn Leu Val Ala Ala Gly Ser Glu Ala Ser Asp Arg
                260                 265                 270

Val Arg Gln Val Leu Met Val Met Val Leu Leu Ala Ser Ala Asn Cys
    275                 280                 285

Val Leu Asp Pro Leu Val Tyr Tyr Phe Ser Ala Glu Gly Phe Arg Asn
    290                 295                 300

Thr Leu Arg Gly Leu Gly Thr Trp His Arg Ala Arg Thr Leu Ala Thr
305                 310                 315                 320

Asn Gly Ala Gln Gly Ala Leu Ala Glu Arg Leu Thr Glu Thr Thr Cys
                325                 330                 335

Ile Ala Gly Pro Ala Pro Ala Ser Arg Glu Pro Pro Ala Ser Ser Pro
                340                 345                 350

Gly Gly Thr Pro Leu Thr Gln Arg Arg Glu Asp Ser Ala Leu
                355                 360                 365

<210> SEQ ID NO 6
<211> LENGTH: 372
<212> TYPE: PRT
<213> ORGANISM: Homo sapiens

<400> SEQUENCE: 6

Met Leu Ala Asn Ser Ser Thr Asn Ser Ser Val Leu Pro Cys Pro
 1               5                  10                  15

Asp Tyr Arg Pro Thr His Arg Leu His Leu Val Val Tyr Ser Leu Val
                 20                  25                  30

Leu Ala Ala Gly Leu Pro Leu Asn Ala Leu Ala Leu Trp Val Phe Leu
             35                  40                  45

Arg Ala Leu Arg Val His Ser Val Val Ser Val Tyr Met Cys Asn Leu
 50                  55                  60

```
Ala Ala Ser Asp Leu Leu Phe Thr Leu Ser Leu Pro Val Arg Leu Ser
 65                  70                  75                  80

Tyr Tyr Ala Leu His His Trp Pro Phe Pro Asp Leu Leu Cys Gln Thr
                 85                  90                  95

Thr Gly Ala Ile Phe Gln Met Asn Met Tyr Gly Ser Cys Ile Phe Leu
                100                 105                 110

Met Leu Ile Asn Val Asp Arg Tyr Ala Ala Ile Val His Pro Leu Arg
                115                 120                 125

Leu Arg His Leu Arg Arg Pro Arg Val Ala Arg Leu Leu Cys Leu Gly
        130                 135                 140

Val Trp Ala Leu Ile Leu Val Phe Ala Val Pro Ala Ala Arg Val His
145                 150                 155                 160

Arg Pro Ser Arg Cys Arg Tyr Arg Asp Leu Glu Val Arg Leu Cys Phe
                165                 170                 175

Glu Ser Phe Ser Asp Glu Leu Trp Lys Gly Arg Leu Leu Pro Leu Val
                180                 185                 190

Leu Leu Ala Glu Ala Leu Gly Phe Leu Leu Pro Leu Ala Ala Val Val
        195                 200                 205

Tyr Ser Ser Gly Arg Val Phe Trp Thr Leu Ala Arg Pro Asp Ala Thr
        210                 215                 220

Gln Ser Gln Arg Arg Arg Lys Thr Val Arg Leu Leu Leu Ala Asn Leu
225                 230                 235                 240

Val Ile Phe Leu Leu Cys Phe Val Pro Tyr Asn Ser Thr Leu Ala Val
                245                 250                 255

Tyr Gly Leu Leu Arg Ser Lys Leu Val Ala Ala Ser Val Pro Ala Arg
                260                 265                 270

Asp Arg Val Arg Gly Val Leu Met Val Met Val Leu Leu Ala Gly Ala
                275                 280                 285

Asn Cys Val Leu Asp Pro Leu Val Tyr Tyr Phe Ser Ala Glu Gly Phe
                290                 295                 300

Arg Asn Thr Leu Arg Gly Leu Gly Thr Pro His Arg Ala Arg Thr Ser
305                 310                 315                 320

Ala Thr Asn Gly Thr Arg Ala Ala Leu Ala Gln Ser Glu Arg Ser Ala
                325                 330                 335

Val Thr Thr Asp Ala Thr Arg Pro Asp Ala Ala Ser Gln Gly Leu Leu
                340                 345                 350

Arg Pro Ser Asp Ser His Ser Leu Ser Ser Phe Thr Gln Cys Pro Gln
                355                 360                 365

Asp Ser Ala Leu
                370
```